United States Patent [19]

McClelland et al.

[11] Patent Number: 5,543,328
[45] Date of Patent: Aug. 6, 1996

[54] ADENOVIRUSES HAVING MODIFIED FIBER PROTEINS

[75] Inventors: Alan McClelland, Gaithersburg; Susan C. Stevenson, Federick, both of Md.

[73] Assignee: Genetic Therapy, Inc., Gaithersburg, Md.

[21] Appl. No.: 106,078

[22] Filed: Aug. 13, 1993

[51] Int. Cl.$^6$ .......................... C12N 15/86; C12N 15/62; C12N 15/34; A61K 48/00
[52] U.S. Cl. .................... 435/320.1; 424/93.1; 424/93.2; 536/23.4; 536/23.72; 935/22; 935/32; 935/57
[58] Field of Search ........................ 435/320.1; 424/93.1, 424/93.2; 536/23.4, 23.72; 935/22, 32, 57

[56] References Cited

FOREIGN PATENT DOCUMENTS

WO94/10323  5/1994  WIPO.

OTHER PUBLICATIONS

B. N. Fields et al., Eds. *Fundamental Virology*, 2nd Ed. New York: Raven Press, 1991, p. 779.
F. Levine et al. (1993) Am. J. Dis. Child 147(11):1167–1174.
D. Jolly (1994) Cancer Gene Therapy 1(1):51–64.
M. A. Kay et al. (1994) Proc. Natl. Acad. Sci. USA 91:2353–2357.
K. F. Kozarsky et al. (1994) J. Biol. Chem. 269:13695–13702.
T. A. G. Smith et al. (1993) Nature Genetics 5:397–402.
S. Connelly et al.. (1995) Human Gene Therapy 6:185–193.
V. Descamps et al. (1994) Human Gene Therapy 5:979–985.
L. D. Stratford–Perricaudet et al. (1990) Human Gene Therapy 1:241–256.
F. D. Ledley Human Gene Therapy (1991) 2:77–83.

*Primary Examiner*—Mindy Fleisher
*Assistant Examiner*—Johnny F. Railey, II
*Attorney, Agent, or Firm*—Elliot M. Olstein; Raymond J. Lillie

[57] ABSTRACT

An adenovirus wherein the adenovirus fiber protein includes a ligand which is specific for a receptor located on a desired cell type. The adenovirus may have at least a portion of the adenovirus fiber protein removed and replaced with a ligand which is specific for a receptor located on a desired cell type, or the adenovirus may include a fusion protein of the adenovirus fiber protein and the ligand. Such an adenovirus may also include a gene(s) encoding a therapeutic agent(s) and may be "targeted" in order to deliver such gene(s) to a desired cell type.

35 Claims, 21 Drawing Sheets

```
   1  AGTTTATGCA GCGGGTGAAC ATGATCATGG CAGAATCACC AGGCCTCATC ACCATCTGCC
  61  TTTTAGGATA TCTACTCAGT GCTGAATGTA CAGTTTTTCT TGATCATGAA AAGCCAACA
 121  AAATTCTGAA TCGGCCAAAG AGTATAATT CAGGTAAATT GGAAGAGTTT GTTCAAGGA
 181  ACCTTGAGAG AGAATGTATG GAAGAAAAGT GTAGTTTTGA AGAAGGACGA GAAGTTTTG
 241  AAAACACTGA AGAACAACT GAATTTTGGA ACCAGTATGT TGATGAGAT CAGTGTGAGT
 301  CCAATCCATG TTTAAATGGC GGCAGTTGCA AGGATGACAT TAATTCCTAT GAATGTTGT
 361  GTCCCTTTGG ATTTGAAGGA AAGAACTGTG AATTAGATGT AACATGTAAC ATTAAGAATG
 421  GCAGATGCGA GCAGTTTGT AAAAATAGTG CTGATAACAA GGTGGTTTGC TCGTGTACTG
 481  AGGGATATCG ACTTGCAGAA AACCAGAAGT CCTGTGAACC AGCAGTGCCA TTTCCATGTG
 541  GAAGAGTTTC TGTTTCACAA ACTTCTAACC TCACCCGTGC TGAGACTGTT TTTCCTGATG
 601  TGGACTATGT AAATTCTACT GAAGCTGAAA CCATTTTGGA TAACATCACT CAAAGCACCC
 661  AATCATTTAA TGACTTCACT CGGGTTGTTG GTGGAGAAGA GTGGAGAGGA TGGGAGGCTCT
 721  CTTGGCAGGT TGTTTTGAAT GTTAAGTTG ATGCATTCTG TGGAGCCTCT TTGATCGAT TTAAATT ACAGTGTCG
 781  AAAATGGAT TGTAACTGCT GCCCACTGTG TTGAAAGTGG TGTTAAAATT ACAGTGTCG
 841  CAGGTGAACA TAATATTGAG GAGACAGAAC ATAGAAGTA AAAGGAAAT GTGATTCGAA
 901  TTATTCCTCA CCACAACTAC AATGCAGCTA TTAATAAGTA CAACCATGAC ATTGCCCTTC
 961  TGGAAGTGGA CGAACCCTTA GTGCTAAACA GCTACGTTAC ACCTATTTGC ATTGCTGACA
1021  AGGAATACAC GAACATCTTC CTCAAATTTG GATCTGGCTA TGTAAGTGGC TGGGAAGAG
1081  TCTTCCACAA AGGGAGATCA GCTTAGTTC TTCAGTACCT TAGAGTTCCA CTTGTTGACC
1141  GAGCCACATG TCTTCGATCT ACAAAGTTCA CCATCTATAT CAACATGTTC TGTGCTGGCT
1201  TCCATGAAGG AGGTAGAGAT TCATGTCAAG GAGATAGTGG GGACCCCCAT GTTACTGAAG
1261  TGGAAGGGAC CAGTTCTTA ACTGGAATTA AGGTAGTTCC TGAAGAGTGT GCAATGAAAG
1321  GCAAATATGG AATATATACC AAGGTATCCC GGTAGTCAA CTGGATTAAG GAAAAAACAA
1381  AGTCACTTA ATGAAAGATG GATTTCCAAG GTTAATTGAT TGGAATTGAA AATTAACAGG
1441  GCCTCTCACT AACTAATCAC TTTCCCATCT TTGTTTAGAT TTGAATATAT ACATTCTATG
1501  ATCATTGCTT TTTCTCTTTA CAGGGGAGAA TACCTGAG
```

FIG. 20

ADENOVIRUSES HAVING MODIFIED FIBER PROTEINS

This invention relates to adenoviruses as used as gene delivery vehicles. More particularly, this invention relates to adenoviruses having fiber proteins which are modified such that the fiber protein includes a ligand which enables the adenovirus to be targeted to a desired cell type.

Adenovirus genomes are linear, double-stranded DNA molecules about 36 kilobase pairs long. Each extremity of the viral genome has a short sequence known as the inverted terminal repeat (or ITR), which is necessary for viral replication. The well-characterized molecular genetics of adenovirus render it an advantageous vector for gene transfer. The knowledge of the genetic organization of adenoviruses allows substitution of large fragments of viral DNA with foreign sequences. In addition, recombinant adenoviruses are structurally stable and no rearranged viruses are observed after extensive amplification.

Adenoviruses may be employed as delivery vehicles for introducing desired genes into eukaryotic cells. The adenovirus delivers such genes to eukaryotic cells by binding cellular receptors. The adenovirus fiber protein is responsible for such attachment. (Philipson, et al., *J. Virol.*, Vol. 2, pgs. 1064–1075 (1968)). The fiber protein consists of two domains—a rod-like shaft portion and a globular head portion which contains the putative receptor binding region. The fiber spike is a homotrimer, and there are 12 spikes per virion. Human adenoviruses may bind to and infect a broad range of cultured cell lines and primary tissues from different species.

It is an object of the present invention to provide an adenovirus which can be targeted to a desired cell type.

In accordance with an aspect of the present invention, there is provided an adenovirus wherein the adenovirus fiber includes a ligand which is specific for a receptor located on a desired cell type.

In one embodiment, at least a portion of the adenovirus fiber protein is removed and replaced with a ligand which is specific for a receptor located on a desired cell type.

As stated hereinabove, the adenovirus fiber protein includes a head portion and a shaft portion. In one embodiment, at least a portion of the head portion is removed and replaced with a ligand which is specific for a receptor located on a desired cell type. In one embodiment, a portion of the head portion is removed and replaced with a ligand which is specific for a receptor located on a desired cell type. In another embodiment, all of the head portion is removed and replaced with a ligand which is specific for a receptor located on a desired cell type.

In one embodiment, the adenovirus is Adenovirus 3, and amino acid residues 132 to 319 of the fiber (i.e., the fiber head region) of Adenovirus 3 are removed and are replaced with a ligand which is specific for a receptor located on a desired cell type. The DNA encoding the fiber protein of Adenovirus 3 is registered as Genbank accession #M12411, (incorporated herein by reference). In another embodiment, the adenovirus is Adenovirus 5, and amino acid residues 400 to 581 of the fiber (i.e., the fiber head region) of Adenovirus 5 are removed and are replaced with a ligand. The DNA encoding the fiber protein of Adenovirus 5 is registered as Genbank accession #M18369, (incorporated herein by reference). In yet another embodiment, the adenovirus is Adenovirus 41, and amino acid residues 387 to 563 of the long fiber (i.e., the fiber head region) of Adenovirus 41 are removed and replaced with a ligand. In a further embodiment, the adenovirus is Adenovirus 41, and amino acid residues 231 to 387 of the short fiber (i.e., the fiber head region) of Adenovirus 41 short are removed and replaced with a ligand. The DNA encoding the Adenovirus 41 long and short fibers is registered as Genbank accession #X17016, incorporated herein by reference.

Ligands which may replace a portion of the adenovirus fiber protein include, but are not limited to, tumor necrosis factors (or TNF's) such as, for example, TNF-alpha and TNF-beta; transferrin, which binds to the transferrin receptor located on tumor cells, activated T-cells, and neural tissue cells; ApoB, which binds to the LDL receptor of liver cells; alpha-2-macroglobulin, which binds to the LRP receptor of liver cells; alpha-1 acid glycoprotein, which binds to the asialoglycoprotein receptor of liver; mannose-containing peptides, which bind to the mannose receptor of macrophages; sialyl-Lewis-X antigen-containing peptides, which bind to the ELAM-1 receptor of activated endothelial cells; CD34 ligand, which binds to the CD34 receptor of hematopoietic progenitor cells; CD40 ligand, which binds to the CD40 receptor of B-lymphocytes; ICAM-1, which binds to the LFA-1 (CD11b/CD18) receptor of lymphocytes, or to the Mac-1 (CD11a/CD18) receptor of macrophages; M-CSF, which binds to the c-fms receptor of spleen and bone marrow macrophages; circumsporozoite protein, which binds to hepatic *Plasmodium falciparum* receptor of liver cells; VLA-4, which binds to the VCAM-1 receptor of activated endothelial cells; LFA-1, which binds to the ICAM-1 receptor of activated endothelial cells; NGF, which binds to the NGF receptor of neural cells; HIV gp120 and Class II MHC antigen, which bind to the CD4 receptor of T-helper cells; the LDL receptor binding region of the apolipoprotein E (ApoE) molecule; colony stimulating factor, or CSF, which binds to the CSF receptor; insulin-like growth factors, such as IGF-I and IGF-II, which bind to the IGF-I and IGF-II receptors, respectively; Interleukins 1 through 14, which bind to the Interleukin 1 through 14 receptors, respectively; and the Fv antigen-binding domain of an immunoglobulin.

Such adenoviruses may be constructed from adenoviral vectors wherein DNA encoding a portion of the fiber protein of the adenovirus is removed and is replaced with DNA encoding a ligand which is specific for a receptor located on a desired cell type.

In another embodiment, the adenovirus includes a fusion protein of the adenovirus fiber protein and a ligand which is specific for a receptor located on a desired cell type.

Adenovirus fiber proteins which may be included in the fusion protein include, but are not limited to, the Adenovirus 3 fiber protein, the Adenovirus 5 fiber protein, and the Adenovirus 41 long and short fiber proteins. The adenovirus fiber protein may be the complete native fiber protein, or may be a mutated fiber protein. The term "mutated" as used herein means that at least one and no more than 100 amino acid residues of the native adenovirus fiber protein have been changed, or that at least one and no more than 100 amino acid residues of the native adenovirus fiber protein have been deleted from the native adenovirus fiber protein.

Ligands may be selected from those hereinabove described.

Such adenoviruses may be vectors wherein DNA encoding the native or mutated adenoviral fiber protein hereinabove mentioned is fused (i.e., operatively linked) to DNA encoding the ligand.

The adenoviral vector, in general, also includes DNA encoding at least one therapeutic agent. The term "therapeutic" is used in a generic sense and includes treating agents, prophylactic agents, and replacement agents.

DNA sequences encoding therapeutic agents which may be placed into the adenoviral vector include, but are not limited to, DNA sequences encoding tumor necrosis factor (TNF) genes, such as TNF-α; genes encoding interferons such as Interferon-α, Interferon-β, and Interferon-δ; genes encoding interleukins such as IL-1, IL-1β, and Interleukins 2 through 14; genes encoding GM-CSF; genes encoding adenosine deaminase, or ADA; genes which encode cellular growth factors, such as lymphokines, which are growth factors for lymphocytes; genes encoding soluble CD4; Factor VIII; Factor IX; T-cell receptors; the LDL receptor, ApoE, ApoC, ApoAI and other genes involved in cholesterol transport and metabolism; the alpha-1 antitrypsin (αlAT) gene, the ornithine transcarbamylase (OTC) gene, the CFTR gene, the insulin gene, viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, and antisense sequences which inhibit viral replication, such as antisense sequences which inhibit replication of hepatitis B or hepatitis non-A non-B virus.

The DNA sequence encoding at least one therapeutic agent is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; and the ApoAI promoter. It is to be understood, however, that the scope of the present invention is not to be limited to specific foreign genes or promoters.

The adenoviral vector which is employed may, in one embodiment, be an adenoviral vector which includes essentially the complete adenoviral genome. (Shenk, et al., *Curr. Top. Microbiol. Immunol.*, (1984); 111(3):1–39), incorporated herein by reference. Alternatively, the adenoviral vector may be a modified adenoviral vector in which at least a portion of the adenoviral genome has been deleted.

In one embodiment, the adenoviral vector comprises an adenoviral 5' ITR; an adenoviral 3' ITR; an adenoviral encapsidation signal; at least one DNA sequence encoding a therapeutic agent; and a promoter controlling the at least one DNA sequence encoding a therapeutic agent. The vector is free of the adenoviral E1, E2, E3, and E4 DNA sequences, and the vector is free of DNA sequences encoding adenoviral proteins promoted by the adenoviral major late promoter; i.e., the vector is free of DNA encoding adenoviral structural proteins.

Such vectors may be constructed by removing the adenoviral 5' ITR, the adenoviral 3' ITR, and the adenoviral encapsidation signal, from an adenoviral genome by standard techniques. Such components, as well as a promoter (which may be an adenoviral promoter or a non-adenoviral promoter), tripartite leader sequence, poly A signal, and selectable marker, may, by standard techniques, be ligated into a base plasmid or "starter" plasmid such as, for example, pBluescript II KS-(Stratagene), to form an appropriate cloning vector. The cloning vector may include a multiple cloning site to facilitate the insertion of DNA sequence(s) encoding therapeutic agent(s) into the cloning vector. In general, the multiple cloning site includes "rare" restriction enzyme sites; i.e., sites which are found in eukaryotic genes at a frequency of from about one in every 10,000 to about one in every 100,000 base pairs. An appropriate vector is thus formed by cutting the cloning vector by standard techniques at appropriate restriction sites in the multiple cloning site, and then ligating the DNA sequence encoding a therapeutic agent(s) into the cloning vector.

The vector may then be packaged into infectious viral particles using a helper adenovirus which provides the necessary encapsidation materials. Preferably the helper virus has a defective encapsidation signal in order that the helper virus will not encapsidate itself. An example of an encapsidation defective helper virus which may be employed is described in Grable, et al., *J. Virol.*, Vol. 66, pgs. 723–731 (1992).

In another embodiment, the vector comprises an adenoviral 5' ITR; an adenoviral 3' ITR; an adenoviral encapsidation signal; at least one DNA sequence encoding a therapeutic agent(s); and a promoter controlling the DNA sequence(s) encoding a therapeutic agent(s). The vector is free of at least the majority of adenoviral E1 and E3 DNA sequences, but is not free of all of the E2 and E4 DNA sequences, and DNA sequences encoding adenoviral proteins promoted by the adenoviral major late promoter. In one embodiment, the vector is also free of at least a portion of at least one DNA sequence selected from the group consisting of the E2 and E4 DNA sequences. In another embodiment, the vector is free of at least the majority of the adenoviral E1 and E3 DNA sequences, and is free of one of the E2 and E4 DNA sequences, and is free of a portion of the other of the E2 and E4 DNA sequences.

In yet another embodiment, the vector is free of at least the majority of the E1 and E3 DNA sequences, is free of at least a portion of at least one DNA sequence selected from the group consisting of the E2 and E4 DNA sequences, and is free of DNA sequences encoding adenoviral proteins promoted by the adenoviral major late promoter.

Such a vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a tripartite leader sequence, a multiple -cloning site (which may be as hereinabove described); a poly A signal; and a DNA segment which corresponds to a segment of the adenoviral genome. Such DNA segment serves as a substrate for homologous recombination with a modified or mutated adenovirus, and such sequence may encompass, for example, a segment of the adenovirus 5 genome no longer than from base 3329 to base 6246 of the genome. The plasmid may also include a selectable marker and an origin of replication. The origin of replication may be a bacterial origin of replication. Representative examples of such shuttle plasmids include pAVS6, shown in FIG. 9. A desired DNA sequence encoding a therapeutic agent may then be inserted into the multiple cloning site. Homologous recombination is then effected with a modified or mutated adenovirus in which at least the majority of the E1 and E3 adenoviral DNA sequences have been deleted. Such homologous recombination may be effected through co-transfection of the shuttle plasmid and the modified adenovirus into a helper cell line, such as 293 cells, by $CaPO_4$ precipitation. Upon such homologous recombination, a recombinant adenoviral vector is formed which includes DNA sequences derived from the shuttle plasmid between the Not I site and the homologous recombination fragment, and DNA derived from the E1 and E3 deleted adenovirus between the homologous recombination fragment and the 3' ITR.

In one embodiment, the homologous recombination fragment overlaps with nucleotides 3329 to 6246 of the adenovirus 5 genome.

Through such homologous recombination, a vector is formed which includes an adenoviral 5' ITR, an adenoviral encapsidation signal; an E1a enhancer sequence; a promoter; a tripartite leader sequence; at least one DNA sequence encoding a therapeutic agent; a poly A signal; adenoviral DNA free of at least the majority of the E1 and E3 adenoviral DNA sequences; and an adenoviral 3' ITR. This vector may then be transfected into a helper cell line, such as the 293 helper cell line, which will include the E1a and E1b DNA sequences, which are necessary for viral replication, and to generate infectious viral particles.

The vector is transfected into an appropriate cell line for the generation of infectious viral particles wherein the adenovirus fiber includes a ligand which is specific for a receptor located on a desired cell type. Transfection may take place by electroporation, calcium phosphate precipitation, microinjection, or through proteoliposomes.

Examples of appropriate cell lines include, but are not limited to, HeLa cells or 293 (embryonic kidney epithelial) cells. The infectious viral particles may then be administered in vivo to a host. The host may be an animal host, including mammalian hosts and human hosts. Such viral particles are "targetable," i.e., the viral particles, upon administration to the host, will bind to and infect a desired target cell or tissue, and thereby delivering DNA encoding a therapeutic agent to the desired target cell or tissue. The particular target cell or tissue to which the particles are targeted is dependent upon the ligand with which the particle is engineered.

The vector, which consists of an infectious adenovirus particle having a modified fiber protein, is administered in an amount effective to provide a therapeutic effect in a host. In one embodiment, the vector may be administered in an amount of from 1 plaque forming unit to about $10^{14}$ plaque forming units, preferably from about $10^6$ plaque forming units to about $10^{13}$ plaque forming units. The host may be a human or non-human animal host.

Preferably, the infectious vector particles are administered systemically, such as, for example, by intravenous administration (such as, for example, portal vein injection or peripheral vein injection), intramuscular administration, intraperitoneal administration, or intranasal administration.

The vector particles may be administered in combination with a pharmaceutically acceptable carrier suitable for administration to a patient. The carrier may be a liquid carrier (for example, a saline solution), or a solid carrier, such as, for example, microcarrier beads.

The vector particles, which include a fiber which is engineered with a ligand which is specific for a receptor located on a desired cell type, travel directly to the desired cells or tissues upon the in vivo administration of such vector particles to a host, and whereby such vector particles infect the desired cell or tissues.

Cells which may be infected by the infectious viral particles include, but are not limited to, primary cells, such as primary nucleated blood cells, such as leukocytes, granulocytes, monocytes, macrophages, lymphocytes (including T-lymphocytes and B-lymphocytes), totipotent stem cells, and tumor infiltrating lymphocytes (TIL cells); bone marrow cells; endothelial cells; activated endothelial cells; epithelial cells; keratinocytes; stem cells; hepatocytes, including hepatocyte precursor cells; fibroblasts; mesenchymal cells; mesothelial cells; parenchymal cells; vascular smooth muscle cells; brain cells and other neural cells; gut enterocytes; gut stem cells; and myoblasts. The cell which is "targeted" or infected or transduced with the infectious viral particles is dependent upon the ligand with which the infectious viral particle has been engineered.

In one embodiment, the infectious viral particles may be targeted to blood cells, whereby such vector particles infect the blood cells with a gene which directly or indirectly enhances the therapeutic effects of the blood cells. The gene carried by the blood cells can be any gene which allows the blood cells to exert a therapeutic effect that it would not ordinarily have, such as a gene encoding a clotting factor useful in the treatment of hemophilia. The gene can encode one or more products having therapeutic effects. Examples of suitable genes include those that encode cytokines such as TNF, interleukins (interleukins 1–14), interferons ($\alpha$, $\beta$, $\delta$-interferons), T-cell receptor proteins and Fc receptors for antigen-binding domains of antibodies, such as immunoglobulins. Other examples of suitable genes include genes encoding soluble CD4 which is used in the treatment of AIDS and genes encoding $\alpha$-antitrypsin, which is useful in the treatment of emphysema caused by $\alpha$-antitrypsin deficiency.

The infected cells are useful in the treatment of a variety of diseases including but not limited to adenosine deaminase deficiency, sickle cell anemia, thalassemia, hemophilia, diabetes, $\alpha$-antitrypsin deficiency, brain disorders such as Alzheimer's disease, phenylketonuria and other illnesses such as growth disorders and heart diseases, for example, those caused by alterations in the way cholesterol is metabolized and defects of the immune system.

In another embodiment, the vector particles may be targeted to and infect liver cells, and such vector particles may include gene(s) encoding polypeptides or proteins which are useful in prevention and therapy of an acquired or an inherited defect in hepatocyte (liver) function. For example, they can be used to correct an inherited deficiency of the low density lipoprotein (LDL) receptor, and/or to correct an inherited deficiency of ornithine transcarbamylase (OTC), which results in congenital hyperammonemia.

In another embodiment, the viral particles may be targeted to liver cells, whereby the viral particles include a gene encoding a therapeutic agent employed to treat acquired infectious diseases, such as diseases resulting from viral infection. For example, the infectious viral particles may be employed to treat viral hepatitis, particularly hepatitis B or non-A non-B hepatitis. For example, an infectious viral particle containing a gene encoding an anti-sense gene could be employed to infect liver cells to inhibit viral replication. In this case, the infectious viral particle, which includes a vector including a structural hepatitis gene in the reverse or opposite orientation, would be introduced into liver cells, resulting in production in the infected liver cells of an anti-sense gene capable of inactivating the hepatitis virus or its RNA transcripts. Alternatively, the liver cells may be infected with an infectious viral particle including a vector which includes a gene which encodes a protein, such as, for example, $\alpha$-interferon, which may confer resistance to the hepatitis virus.

Alternatively, the vector particles including the modified adenovirus fiber and a gene encoding a desired protein or therapeutic agent may be employed to infect a desired cell line in vitro, whereby the infected cells produce a desired protein or therapeutic agent in vitro.

The invention will now be described with respect to the drawings, wherein:

FIG. 20 is the DNA sequence encoding Factor IX (SEQ ID NO: 15); and

Figure 1:
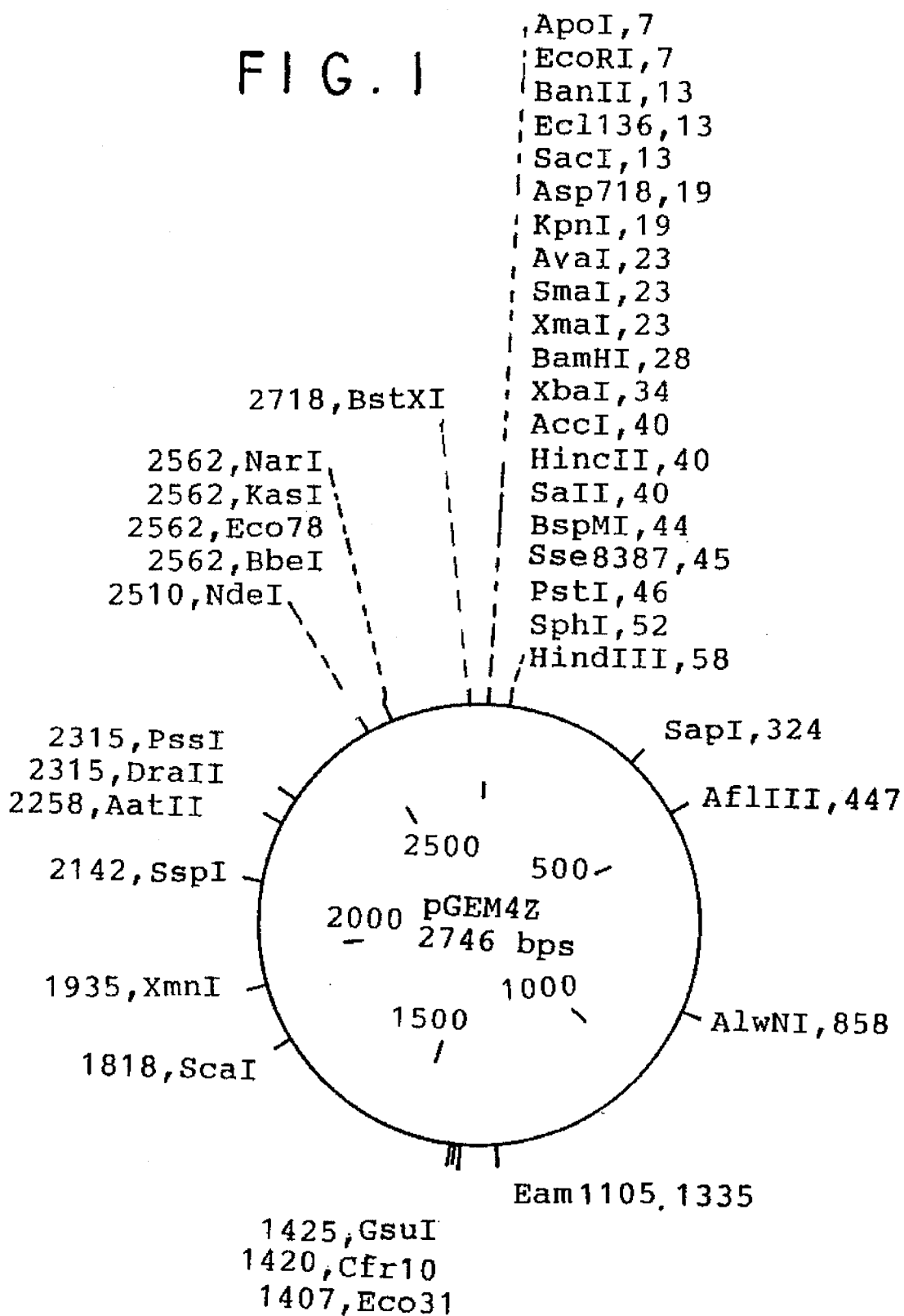
FIG. 1 is a map of the plasmid pGEM4Z.

amplify nucleotides 314 to 787 of the human TNF sequence, Genbank # M10988, incorporated herein by reference. The primers P1 and P4 are designed to add Sal I and XbaI restriction enzyme sites, respectively, for cloning into the expression vector, pGEM4Z. (Promega, FIG. 1) The templates, pGEM5F (FIG. 2) and pT2 (FIG. 4), which contain the correct cDNA for the Adenovirus 5 fiber and human TNF genes, respectively, are used for amplifying the appropriate sequences.

The full length Adenovirus 5 fiber gene was cloned by PCR using the published DNA sequences (Chrobaczek, et al., (1989), Virology, Vol. 161, pgs. 549–554, incorporated herein by reference) to design oligonucleotide primers for amplification from purified genomic DNA. The primers were designed to amplify the entire coding sequence of the full length fiber gene starting from the start codon, ATG, and ending with the termination codon, TAA. The primers, designated, P5 and P6, are as follows:

P5 5'-CATCTGCAGCATGAAGCGCGCAAGACCGTCTGAAGATA-3' (SEQ ID NO: 5)

P6 5'-CAGGAATTCTTATTCTTGGGCAATGTATGAAAAAGTGT-3' (SEQ ID NO: 6)

Figure 2:
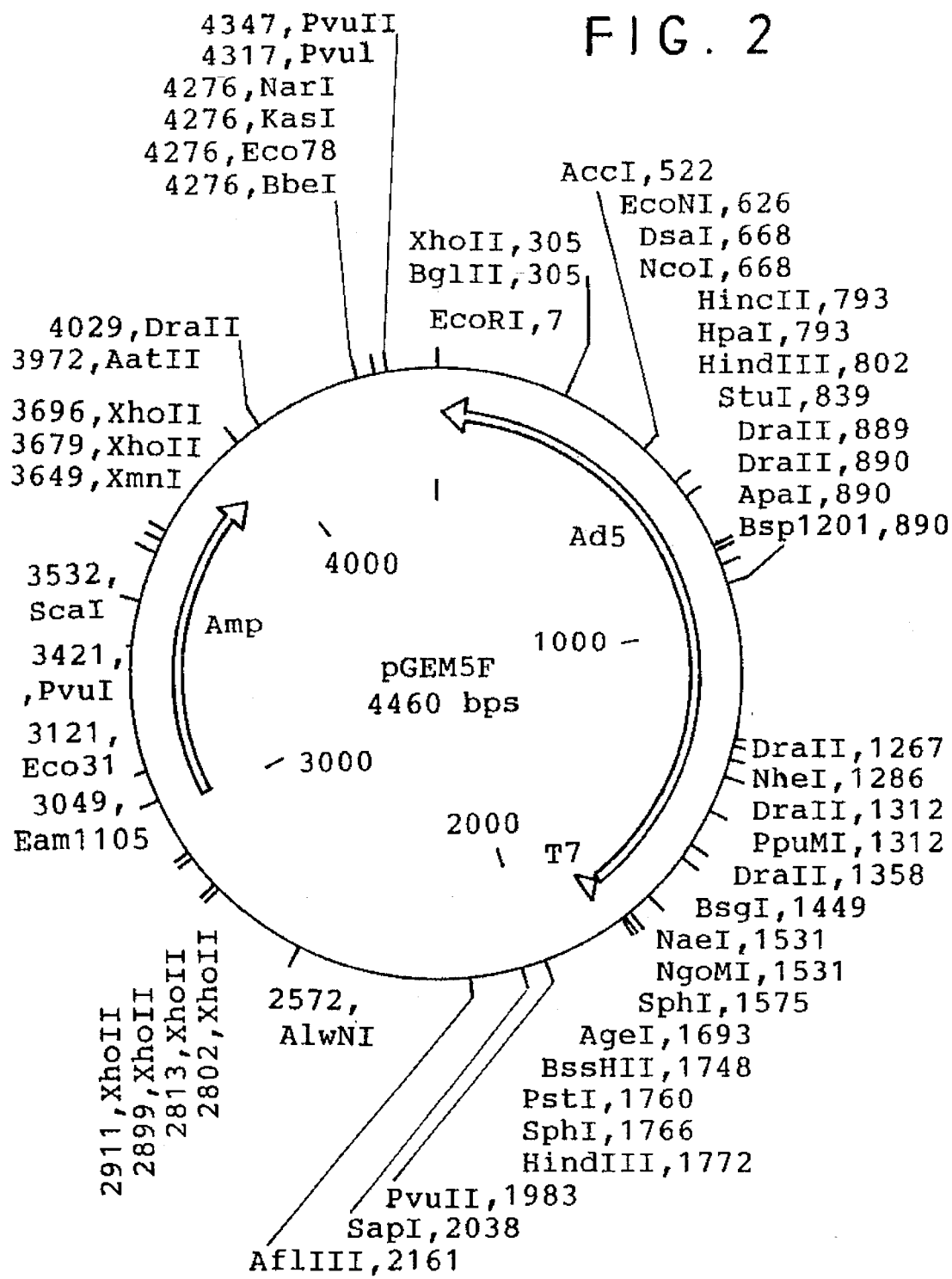
FIG. 2 is a map of the plasmid pGEM5F.

The primers P5 and P6 were designed to contain PstI and EcoRI restriction enzyme sites, respectively, for cloning into the plasmid pGEM4Z. The PCR reaction was carried out as follows: 5 min.—92° C.; then 45 sec.—92° C.; 45 sec.—52° C.; 2 min.—72° C. for 20 cycles, and then 8 min.—72° C. The PCR product then was cut with PstI and EcoRI, and cloned into PstI and EcoRI digested pGEM4Z to form pGEM5F (FIG. 2).

pT2 is formed by cloning the human TNF gene by PCR using primers P7 and P8:

P7 5'-GCAGATCTTTCCGCAGCAGCCGCCACCATGAGCATGAAAGCATC-3' (SEQ ID NO: 7)

P8 5'-GCGTCGACTCGAGTCACAGGGCAATGATCC-3' (SEQ ID NO: 8)

The invention will now be described with respect to the following examples; it is to be understood, however, that the scope of the present invention is not intended to be limited thereby.

EXAMPLE 1

Figure 3:
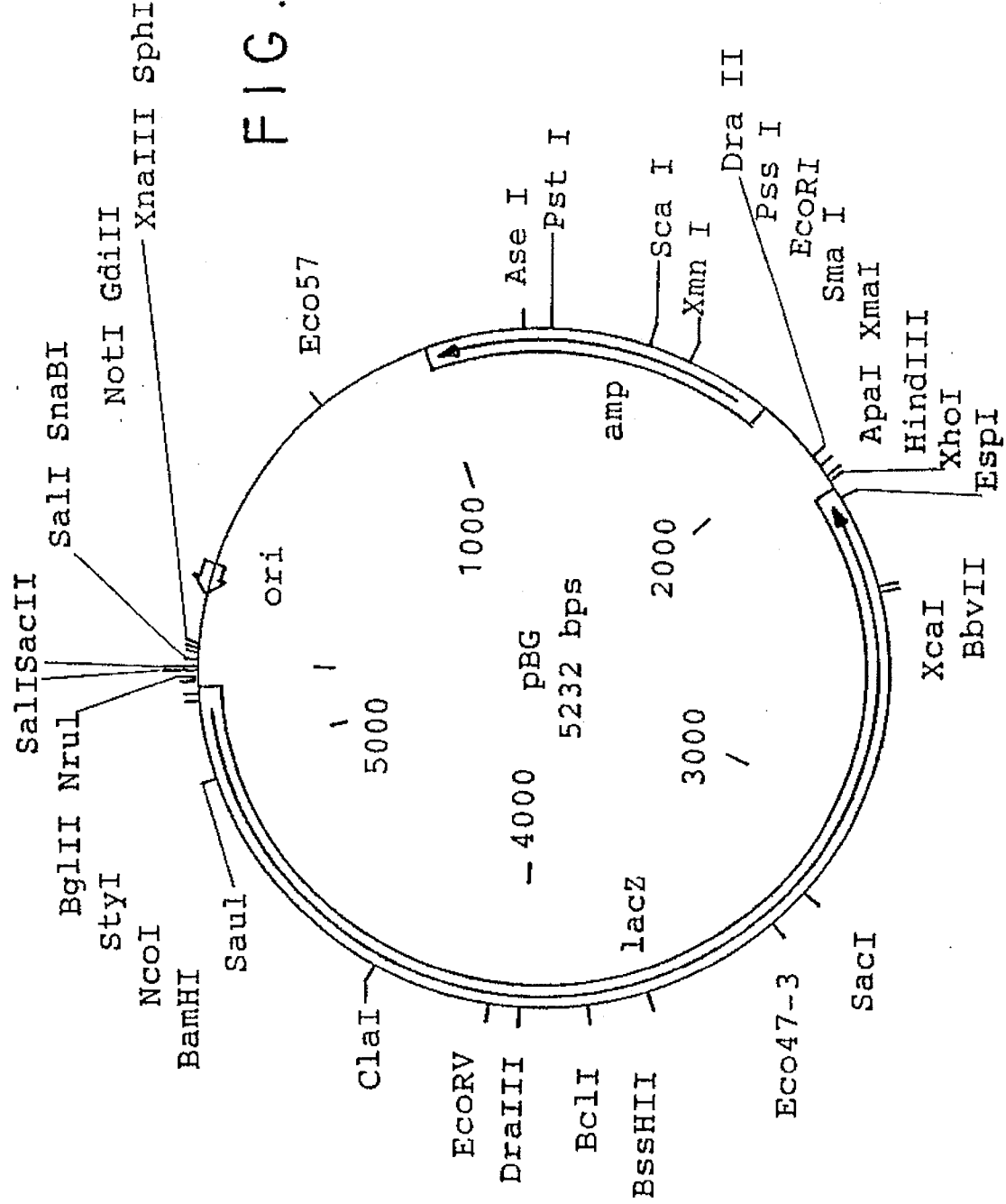
FIG. 3 is a map of the plasmid pBg.
Figure 4:
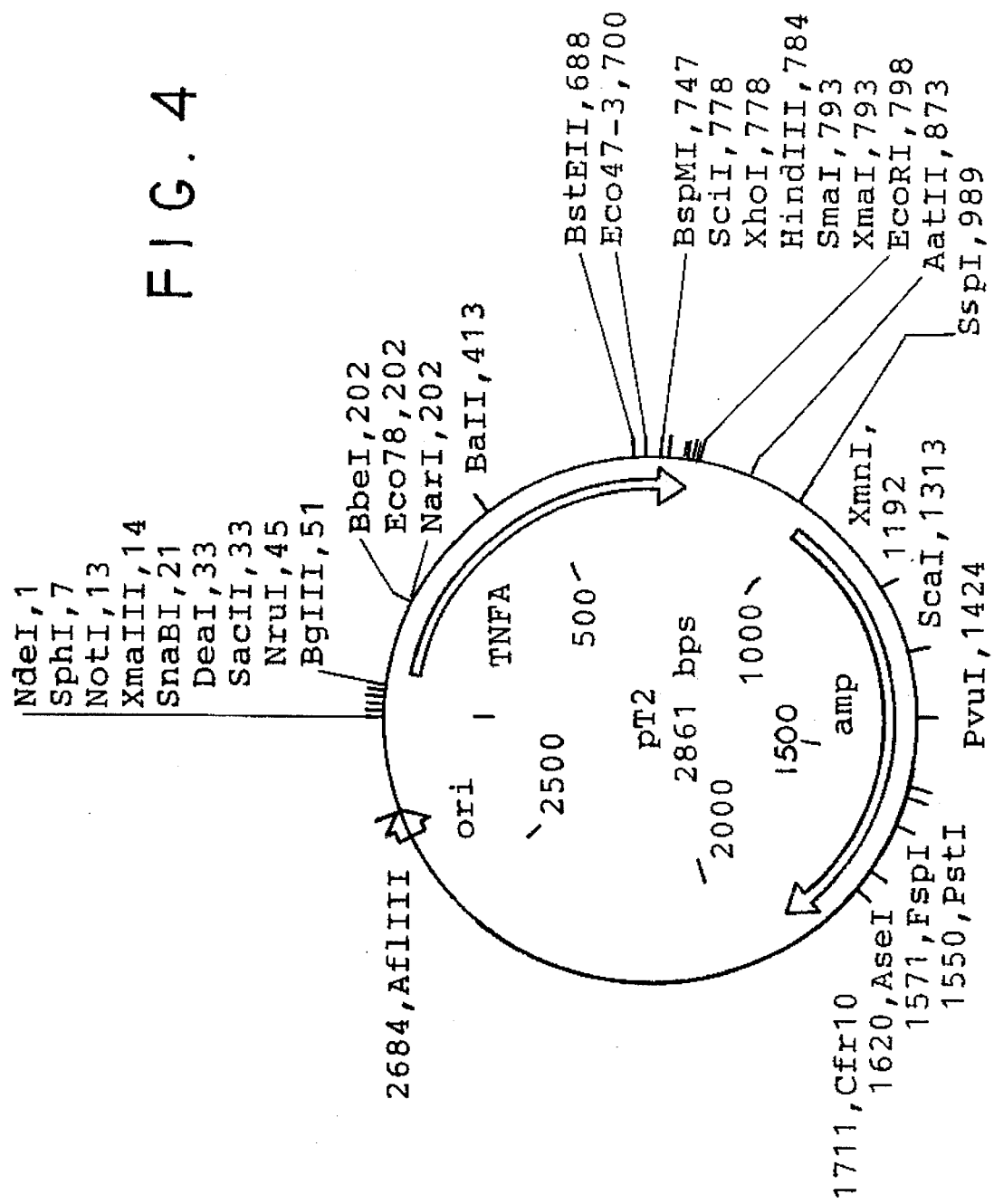
FIG. 4 is a map of the plasmid pT2.

Construction of Adenovirus 5 Including a Chimeric Fiber of Adenovirus 5 Fiber Protein and TNF A. Construction of Vector Including DNA Encoding the Adenovirus 5 Fiber: TNF Chimera The Adenovirus 5 fiber: TNF (5F:TNF) chimera is prepared by PCR gene overlap extension (Horton et al. (1990) Biotechniques 8:528–535, incorporated herein by reference). The Adenovirus 5 fiber tail and shaft regions, amino acids 1 to 399, are connected with the mature TNF protein, amino acids 76 to 233. The primers which are used in the PCR construction are as follows:

based on the published TNF sequence (Wang, et al., Science, Vol 228, pgs 149–154 (1985), (Genbank accession #M10988 incorporated herein by reference). Primers were designed to include BglII and XhoI restriction sites. The PCR product is cut with BglII and XhoI and cloned into BglII and XhoI digested pBg (FIG. 3 and as described in PCT application No. WO91/10728, published Jul. 25, 1991, incorporated herein by reference ) to form pT2. (FIG. 4).

PCR reactions then are carried out using primers P1, P2, P3 and P4 in order to amplify the Adenovirus 5 fiber tail and shaft sequences as well as the mature TNF protein sequence from pGEM5F and pT2, respectively.

The PCR reactions are carried out as follows: 5 min—92° C., then 45 sec—92° C., 45 sec—52° C., 2 min—72° C. for 30 cycles and then 8 min—72° C. The PCR products then are analyzed on a 1% agarose tris/acetate/EDTA gel. The expected 1.2 Kb 5F tail and shaft and the 0.47 Kb TNF fragments are excised from the gel and the second PCR reaction is carried out as described using the primers P1 and 5F P1   5'-CATTGTGTCGACACCATGAAGCGCGCAAGACCGTCTGAA-3' (SEQ ID NO: 1)
   P2   5'-CGGGGTTCGAGAAGATGATCTGACGGTCCACAAAGTTAGCTTATCATT-3' (SEQ ID NO: 2)

TNF P3   5'-GTCA GATC ATCT TCTC GAAC CCCG-3' (SEQ ID NO:3)
    P4   5'-ATGTCTAGATCACAGGGCAATGATCCCAAAGTAGACCTG-3' (SEQ ID NO: 4)

The primers P1 and P2 amplify nucleotides 476 to 1684 of the Adenovirus 5 fiber sequence, Genbank # M18369, incorporated herein by reference. The primers P3 and P4

Figure 5:
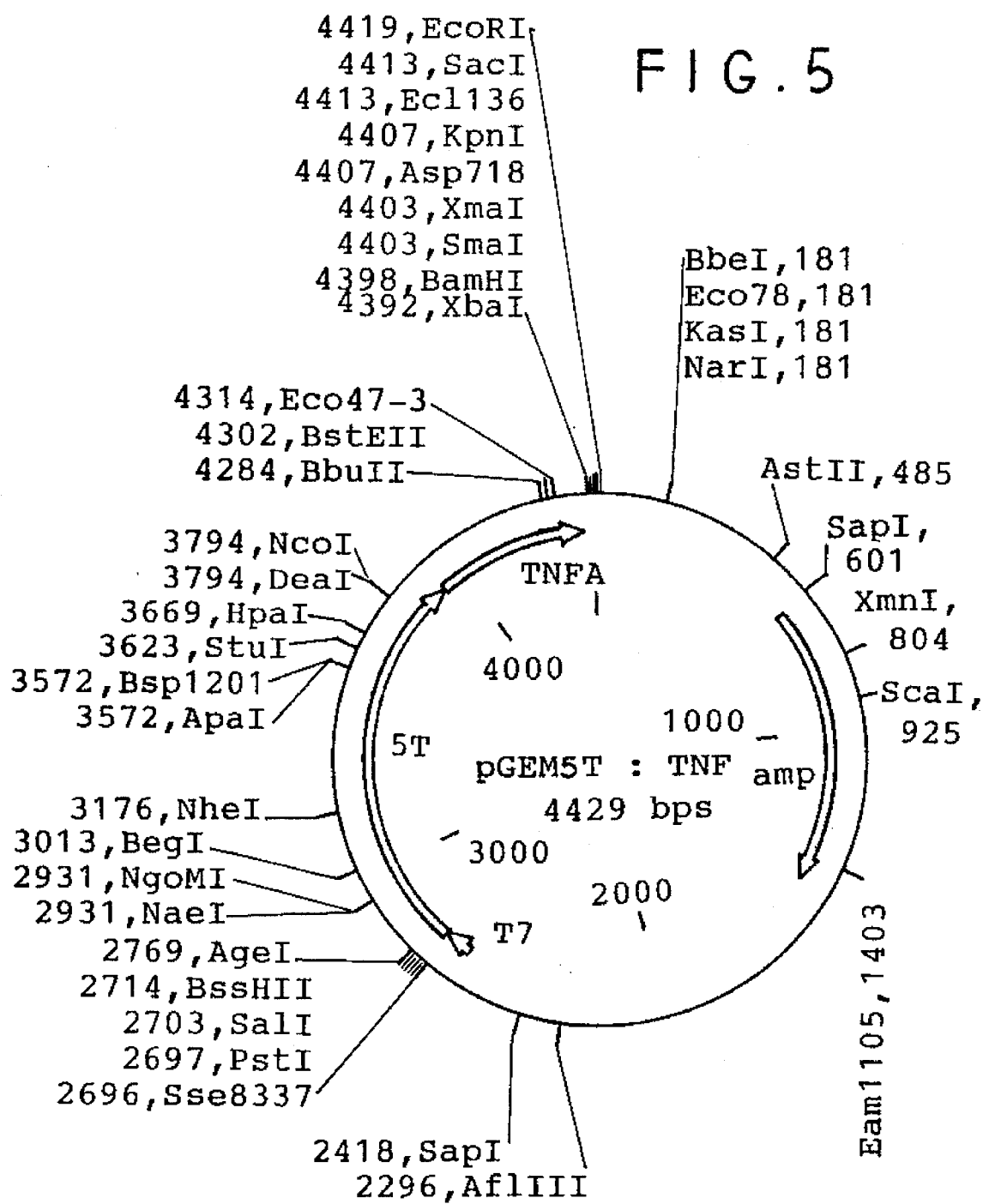
FIG. 5 is a map of the plasmid pGEM5F::TNF.

P4 to amplify the 1.67 Kb full length Adenovirus 5 fiber: TNF chimera. The nucleotide sequence of the cloned insert is determined by DNA sequencing and a clone having a perfect match with the expected sequence can be selected. The insert is cut with SalI and XbaI and cloned into SalI and XbaI digested pGEM4Z to form pGEM5F:TNF (FIG. 5).

B. In vitro Expression and Analysis of the 5F:TNF Chimera

Expression and function of the Adenovirus 5 fiber:TNF chimera is analyzed in an in vitro transcription/translation cell binding experiment using an adaptation of the surface receptor binding assay described by Leone, et al. (1992) Cell. 71:479–488, incorporated herein by reference. A 1 μg aliquot of the pGEM5F:TNF DNA is used in the in vitro transcription/translation reaction (Promega) using [$^{35}$-S] L-methionine. Protein sample preparation for SDS PAGE analysis is carried out such that the trimeric state of the 5F:TNF chimera will remain intact (Novelli et al., (1991) J. Biol. Chem. 266: 9299–9303 incorporated herein by reference.). The translated protein products are analyzed by nondenaturing 4/15% SDS PAGE and fluorography. The expected molecular weights for the 5F:TNF monomer and trimer are approximately 55 kDa and 165 kDa, respectively. Western analysis of the translated protein products demonstrates the correct trimer conformation by reactivity with monoclonal antibodies either specific to Adenovirus 5 fiber trimer, 2A6.36, or to the TNF trimer (Endogen, Inc.). The function of the 5F:TNF trimer then is demonstrated by interaction with the TNF cell surface receptors. A variety of different cell types which express the TNF receptor can be used in this assay such as: HL60 monocyte/macrophages and U937 monocyte/macrophages. Approximately 1×10$^6$ cells are plated onto 60 mm tissue culture dishes and are allowed to attach overnight at 37° C. in a 5% CO$_2$ atmosphere. The labeled protein mixture from the in vitro transcription/translation is applied to the cell surface monolayer and allowed to incubate for one hour at room temperature. The cell surface is washed extensively and the cells are lyzed to analyze cell-associated labeled protein. Samples will be prepared for nondenaturing 4/15% SDS PAGE and fluorography. If the 5F:TNF chimera is functional, the 165 kDa trimer should interact with the TNF receptor.

Specificity of receptor binding is demonstrated through competition analysis using purified human TNF (Endogen, Inc.) and antibodies specific to TNF (Endogen, Inc.) as competitors. A functional 5F:TNF protein which interacts with the TNF receptor will not bind in the presence of excess competitor.

C. Incorporation of 5F:TNF Chimera into Adenovirus

The modified fiber can be incorporated into an intact adenovirus by one of two methods. Both methods utilize a fiber-deleted Adenovirus 5 which is constructed as described in Falgout, et al., J. Virol., Vol. 61, pgs. 3759–3768 (1987), incorporated herein by reference.

In one method, a shuttle vector, pAVS6 (FIG. 9), first is constructed.

Figure 6:
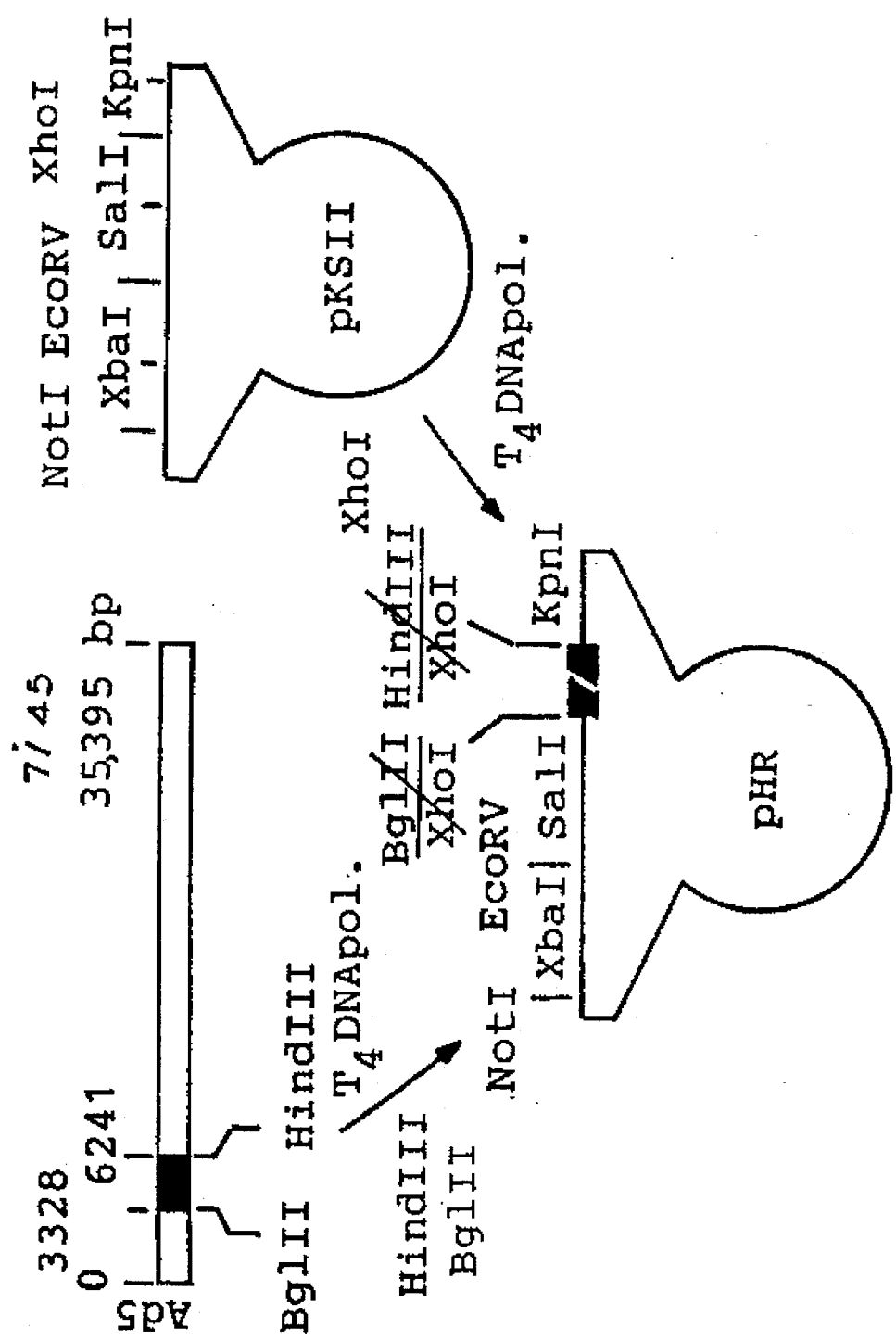
FIG. 6 is a schematic of the construction of the plasmid pHR.

The adenoviral construction shuttle plasmid pAVS6 was constructed in several steps using standard cloning techniques including polymerase chain reaction based cloning techniques. First, the 2913 bp BglII, HindIII fragment was removed from Ad-d1327 and inserted as a blunt fragment into the XhoI site of pKSII⁻ (Stratagene, La Jolla, Calif.) (FIG. 6). Ad-d1327 (Thimmappaya, et al., Cell, Vol. 31, pg. 543 (1983), incorporated herein by reference) is identical to Adenovirus 5 except that an XbaI fragment including bases 28591 to 30474 (or map units 78.5 to 84.7) of the Adenovirus 5 genome, and which is located in the E3 region, has been deleted. The complete Adenovirus 5 genome is registered as Genbank accession #M73260, incorporated herein by reference. The orientation of this fragment was such that the BglII site was nearest the T7 RNA polymerase site of pKSII⁻ and the HindIII site was nearest the T3 RNA polymerase site of pKSII⁻. This plasmid was designated pHR. (FIG. 6).

Figure 7:
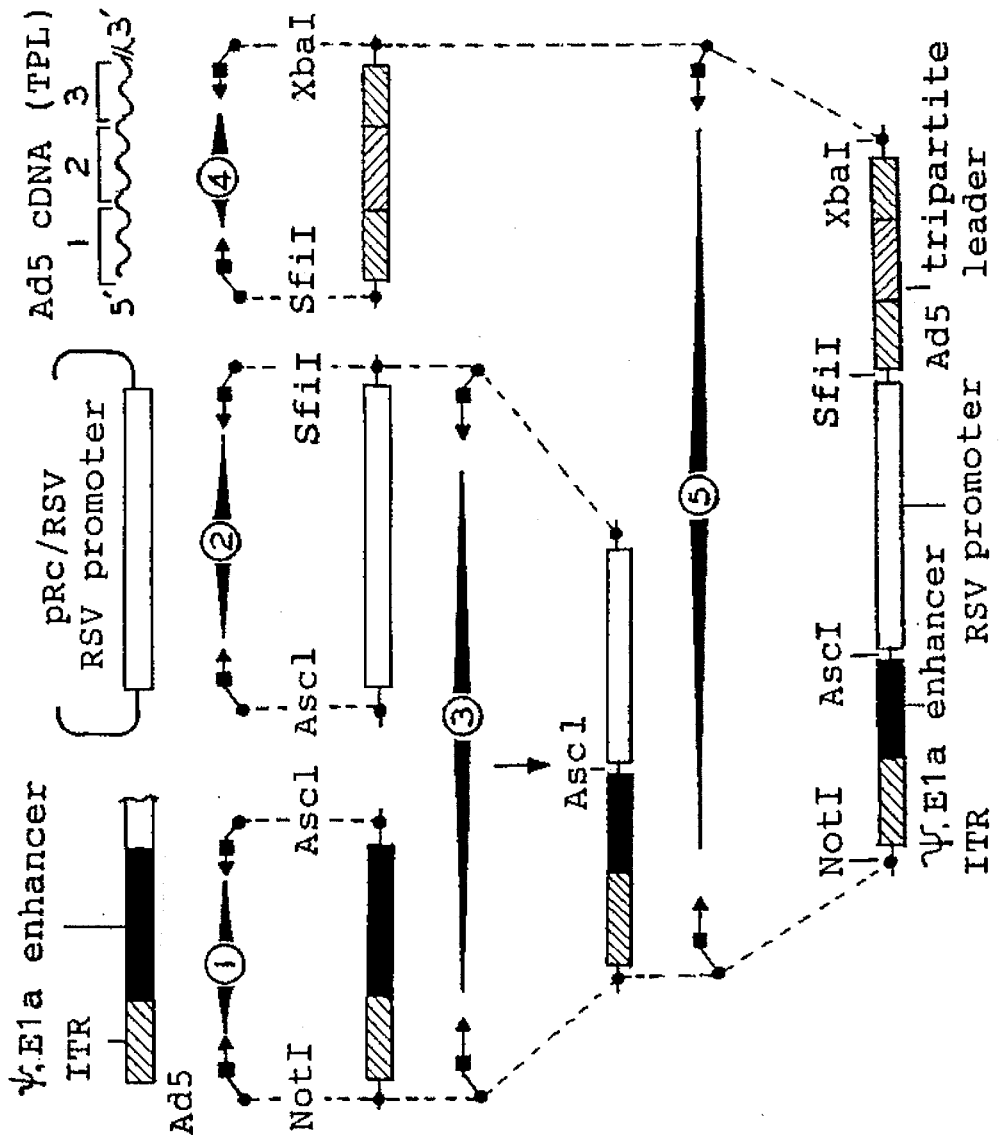
FIG. 7 is a schematic of the construction of a construct including an adenoviral ITR, an encapsidation signal, an E1a enhancer sequence, a Rous Sarcoma Virus promoter, and an Adenovirus 5 tripartite leader sequence.

Second, the ITR, encapsidation signal, Rous Sarcoma Virus promoter, the adenoviral tripartite leader (TPL) sequence and linking sequences were assembled as a block using PCR amplification (FIG. 7). The ITR and encapsidation signal (sequences 1–392 of Ad-d1327 [identical to sequences from Ad5, Genbank accession #M73260], incorporated herein by reference) were amplified (amplification 1) together from Ad-d1327 using primers containing NotI or AscI restriction sites. The Rous Sarcoma Virus LTR promoter was amplified (amplification 2) from the plasmid pRC/RSV (sequences 209 to 605; Invitrogen, San Diego, Calif.) using primers containing an AscI site and an SfiI site. DNA products from amplifications 1 and 2 were joined using the "overlap" PCR method (amplification 3) with only the NotI primer and the SfiI primer. Complementarity between the AscI containing end of each initial DNA amplification product from reactions 1 and 2 allowed joining of these two pieces during amplification. Next the TPL was amplified (amplification 4) (sequences 6049 to 9730 of Ad-d1327 [identical to similar sequences from Ad5, Genbank accession #M73260]) from cDNA made from mRNA isolated from 293 cells (ATCC accession No. CRL 1573) infected for 16 hrs. with Ad-d1327 using primers containing SfiI and XbaI sites respectively. DNA fragments from amplification reactions 3 and 4 were then joined using PCR (amplification 5) with the NotI and XbaI primers, thus creating the complete gene block.

Third, the ITR-encapsidation signal-TPL fragment was then purified, cleaved with NotI and XbaI and inserted into the NotI, XbaI cleaved pHR plasmid. This plasmid was designated pAvS6A and the orientation was such that the NotI site of the fragment was next to the T7 RNA polymerase site (FIG. 8).

Figure 8:
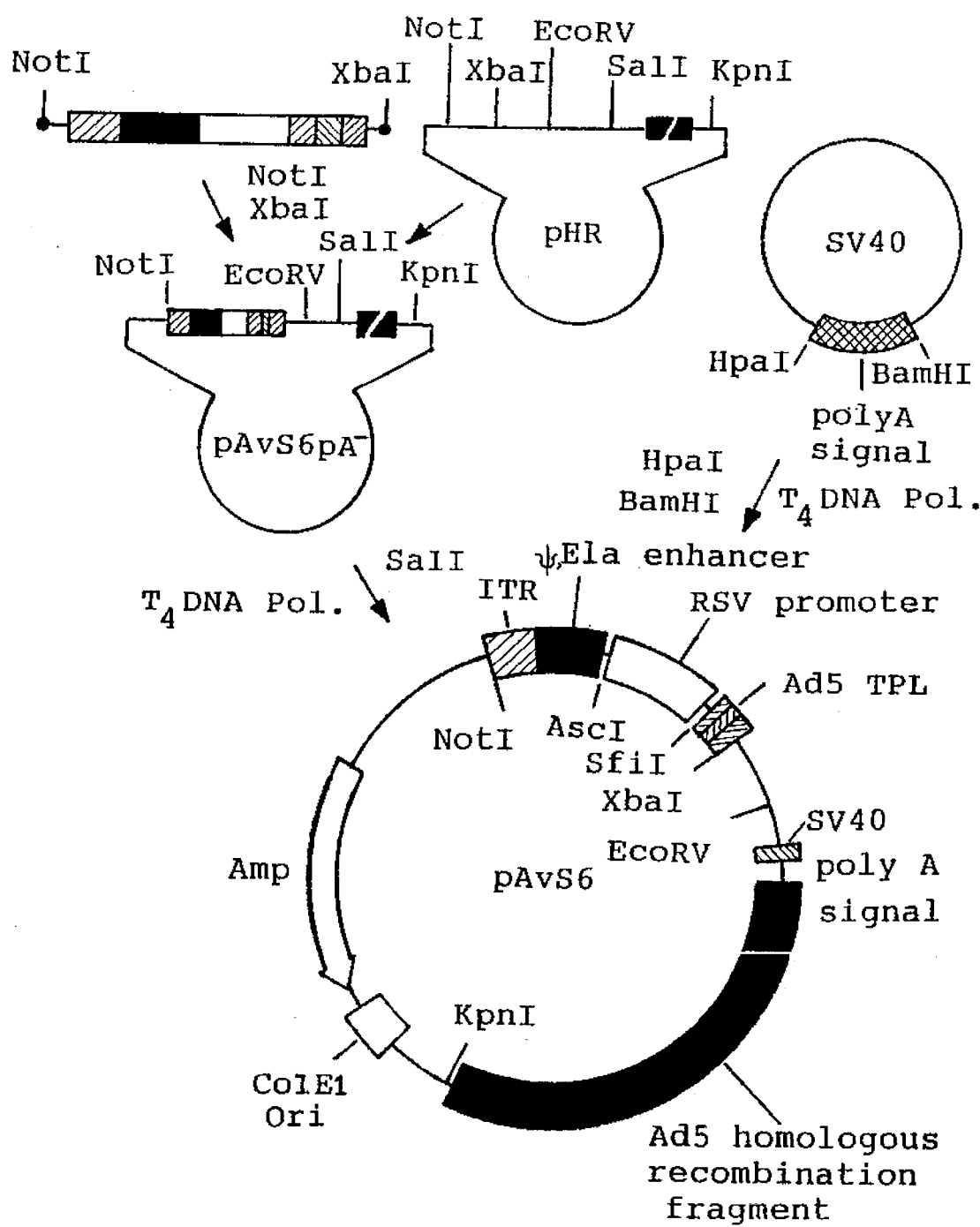
FIG. 8 is a schematic of the construction of plasmid pAVS6.
Figure 9:
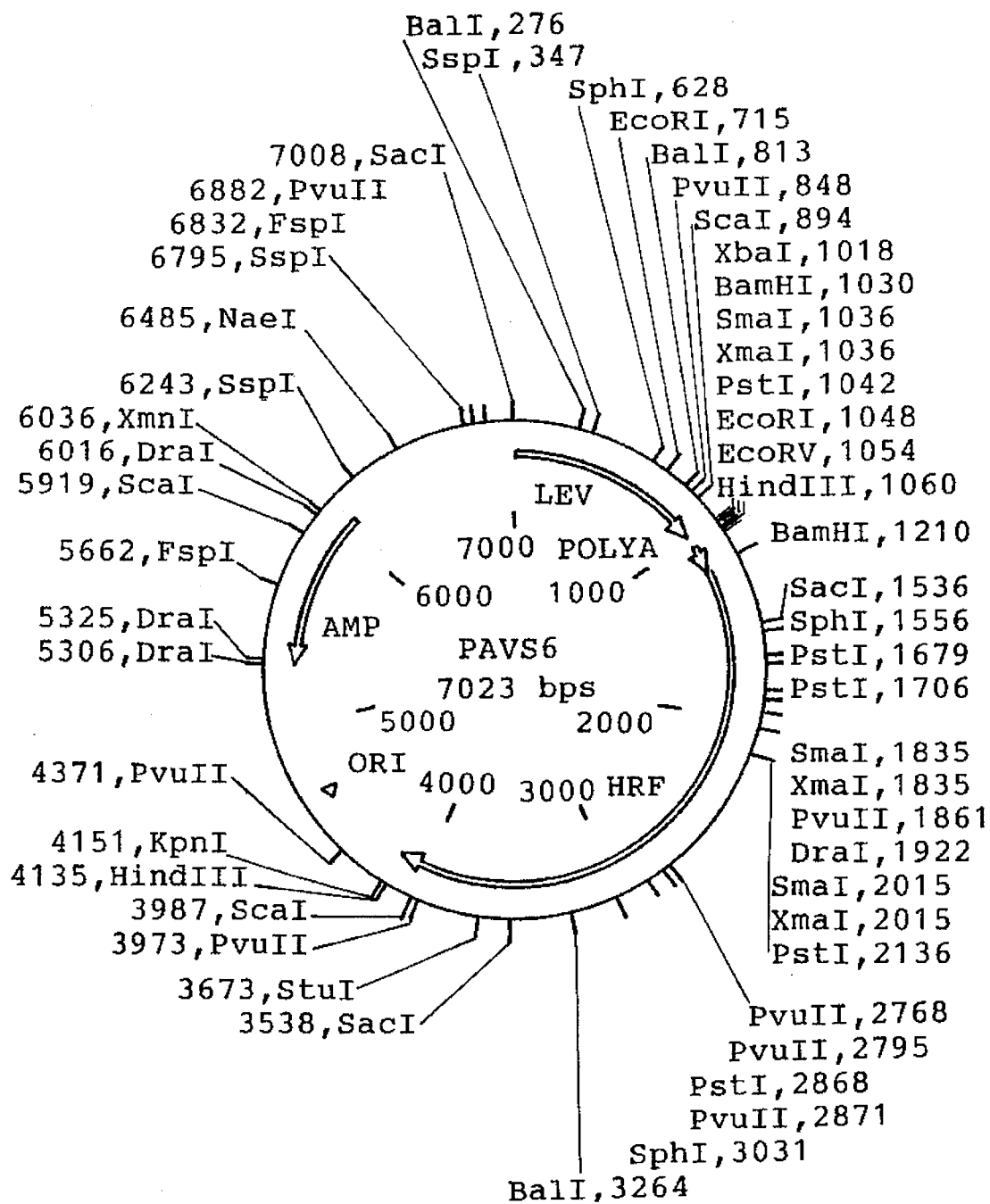
FIG. 9 is a map of plasmid pAVS6.

Fourth, the SV40 early polyA signal was removed from SV40 DNA as an HpaI-BamHI fragment, treated with T4 DNA polymerase and inserted into the SalI site of the plasmid pAvS6A-(FIG. 8) to create pAvS6 (FIGS. 8 and 9).

Figure 10:
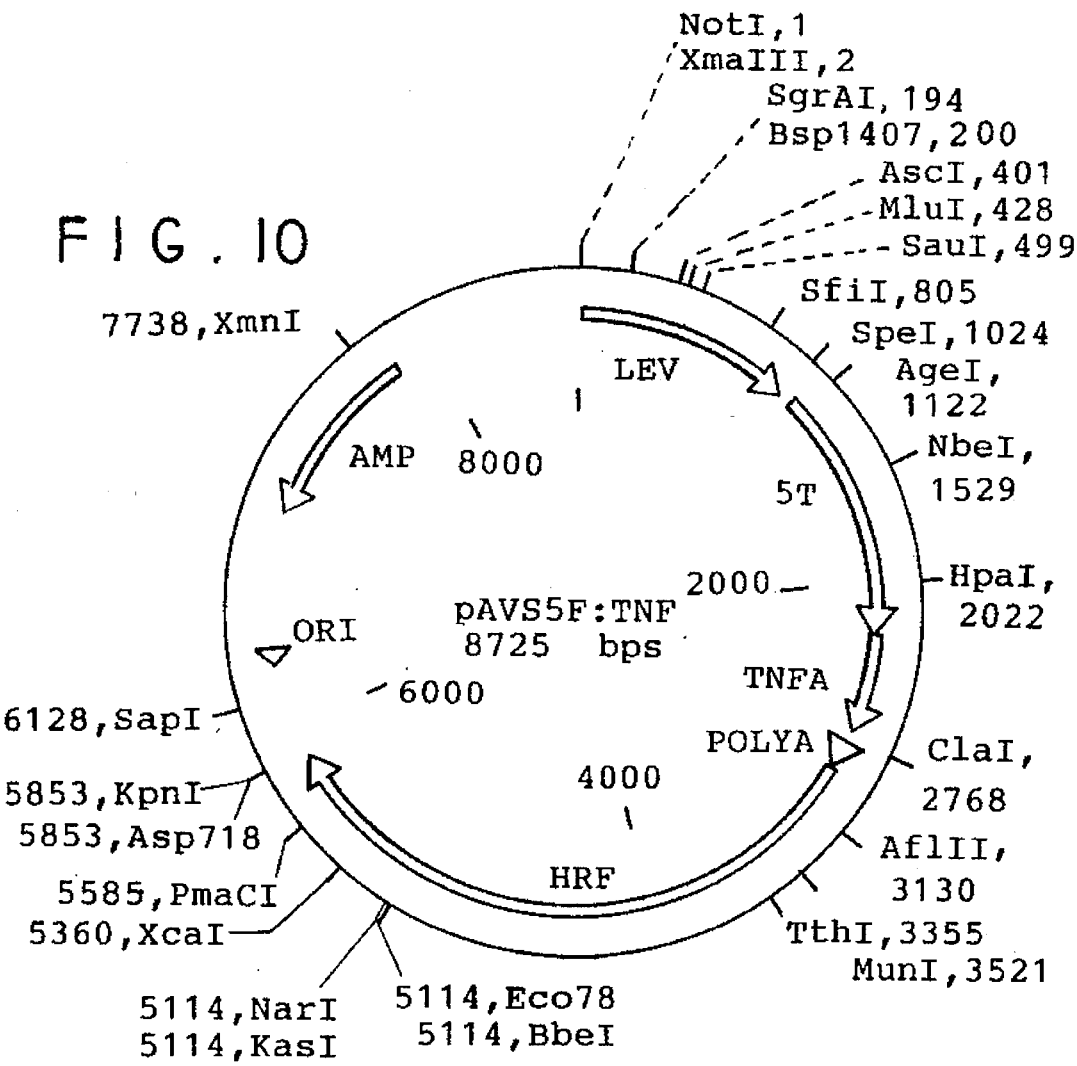
FIG. 10 is a map of plasmid pAVS5F::TNF.

The 5F:TNF chimeric construct then is cloned into pAVS6. The plasmid pGEM5F::TNF is digested with SmaI and SalI to obtain the 5F:TNF fragment. The ends of the fragment are filled in with Klenow DNA polymerase to create a blunt ended 5F:TNF fragment. The blunt ended 5F:TNF fragment then is cloned into EcoRV digested pAVS6 to form pAVS5F::TNF (FIG. 10). pAVS5F::TNF and ClaI digested Ad 5 dl 1021, which is an adenoviral vector wherein DNA encoding the Adenovirus 5 fiber is deleted (Falgout, et al. 1987), are co-transfected into 293 cells using calcium phosphate precipitation. Homologous recombination produces a recombinant adenoviral vector particle containing the 5F:TNF gene.

Figure 11:
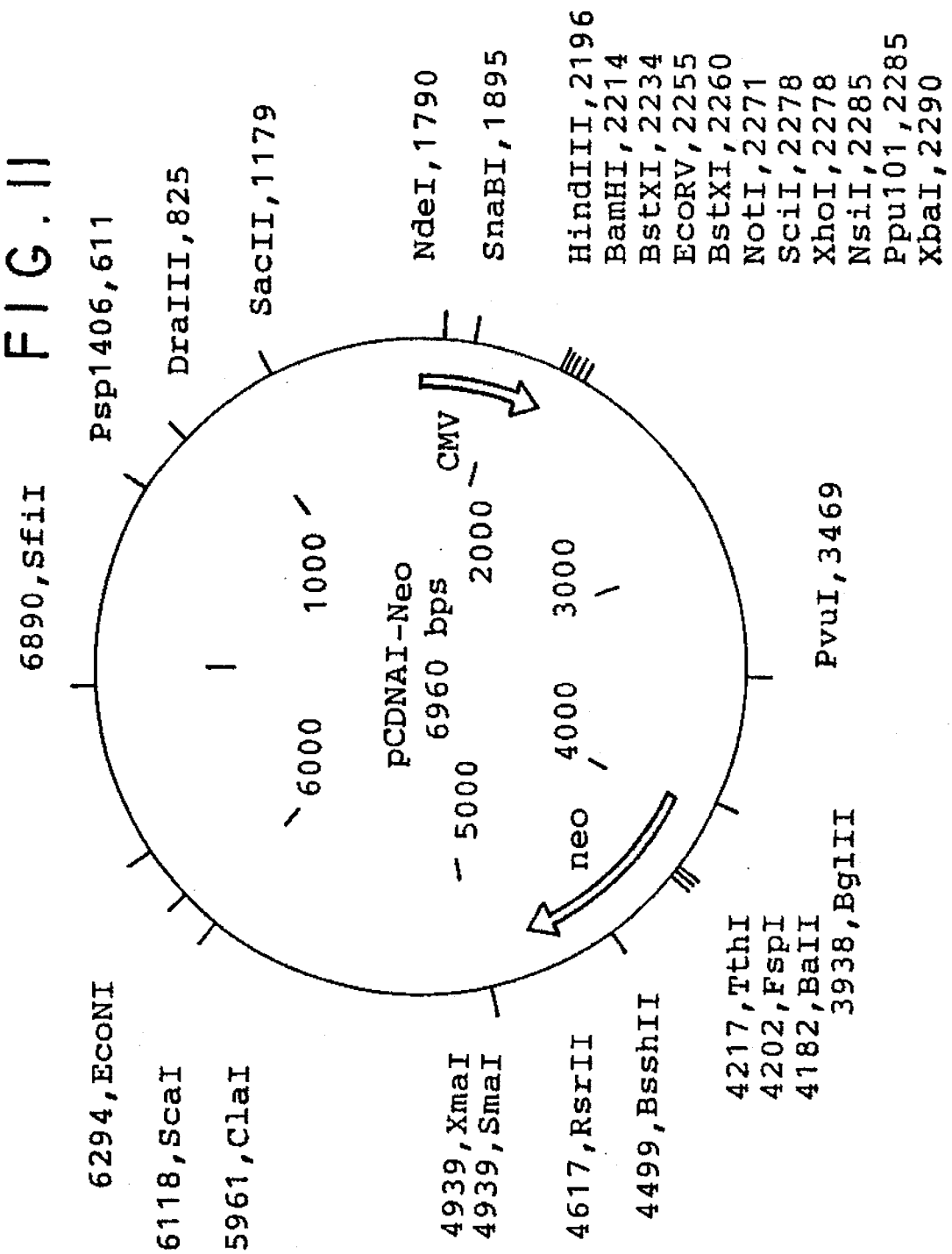
FIG. 11 is a map of plasmid pcDNA-neo.
Figure 12:
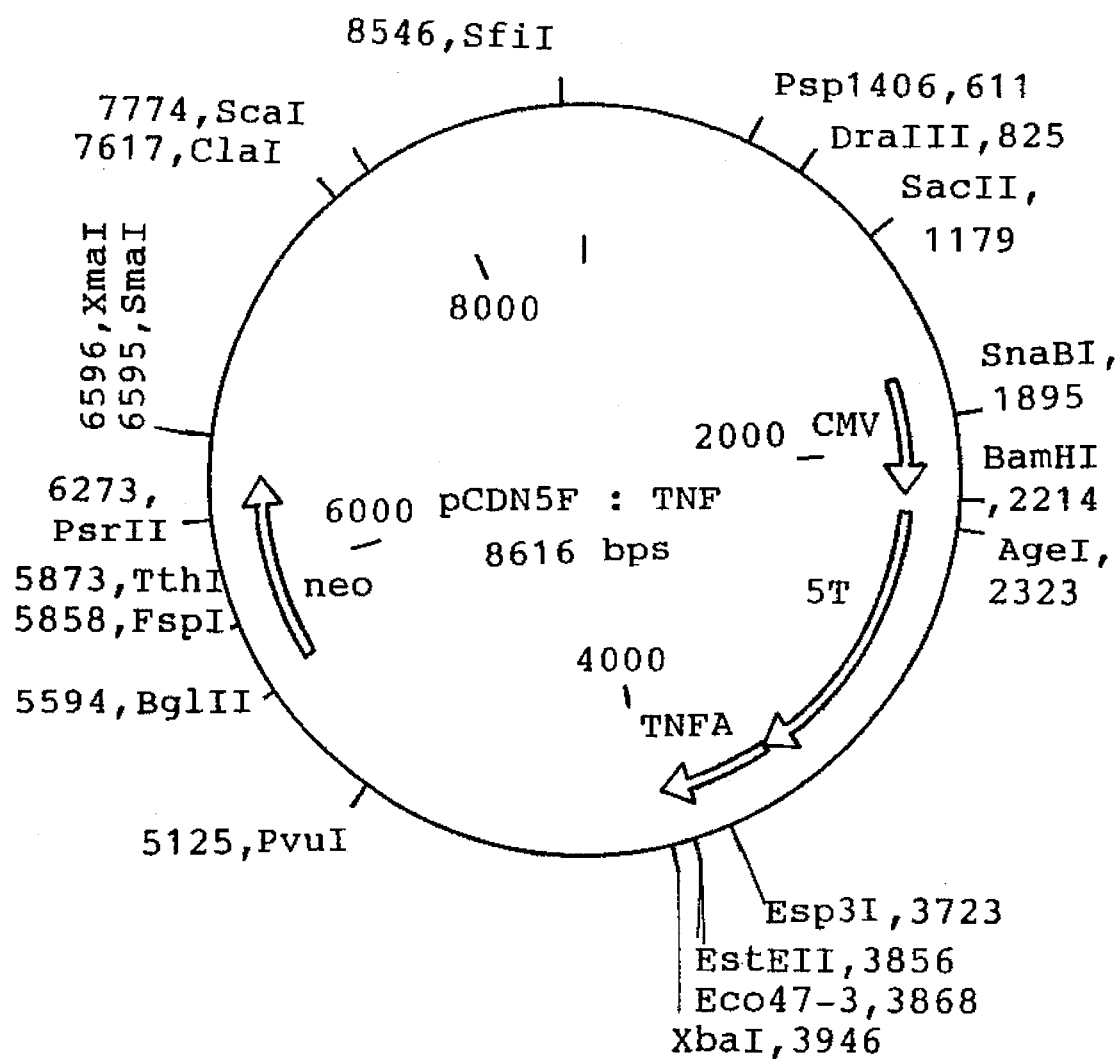
FIG. 12 is a map of plasmid pCDN5F::TNF.
Figure 13:
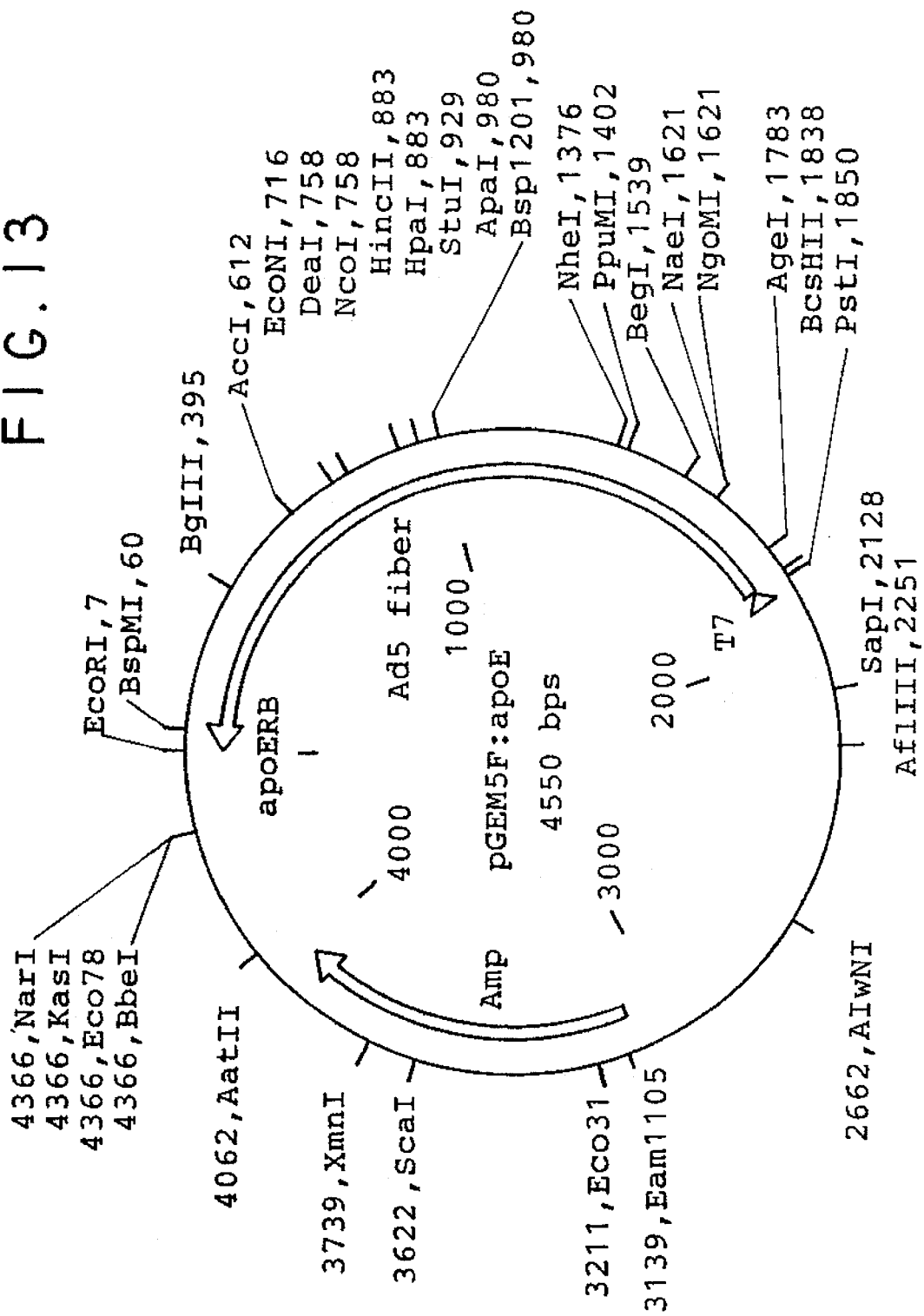
FIG. 13 is a map of plasmid pGEM5F::apoE.

In the second method, pGEM5::TNF is digested with SalI, and the ends of the linearized vector are treated with Klenow DNA polymerase to create blunt ends. The blunt ended, linearized pGEM5F::TNF is digested further with XbaI and cloned into EcoRV and XbaI digested pcDNA-neo (Invitrogen, FIG. 11) to form pcDN5F::TNF. (FIG. 12). pcDN5F::TNF and Ad 5 dl 1021DNA (Falgout, et al., 1987)

are co-transfected into 293 cells using calcium phosphate precipitation to produce a recombinant adenoviral vector particle containing the 5F:TNF fiber protein.

The function of the recombinant 5F:TNF adenovirus is assessed by infection and cell receptor binding assays. To assess virus:TNF receptor interaction and infectivity, plaque assays, cellular receptor binding or competition assays are carried out using the purified virus as the receptor ligand and purified TNF or anti-TNF antibodies as competitors. An infectious recombinant adenovirus expressing 5F:TNF protein which interacts with the TNF receptor will not infect cells in the presence of excess competitor.

For in vitro transduction of cells, an aliquot of the infectious viral particles containing up to about $10^{14}$ plaque forming units, is added to cells expressing a TNF receptor, such as for example, HL60 monocyte/macrophages and U937 monocyte/macrophages, and the viral particles are allowed to bind. For in vivo transduction of cells, an aliquot of the infectious viral particles of up to about $10^{14}$ plaque forming units is administered by intravenous infusion, whereby such infectious viral particles will infect cells expressing a TNF receptor.

EXAMPLE 2

Construction of Adenovirus 5 Including a Chimeric Fiber of Adenovirus 5 Fiber Protein and ApoE

A. Construction of Vector Including DNA Encoding the Adenovirus 5 Fiber:apoE Chimera The Adenovirus 5 fiber:apoE (5F:apoE) chimera is prepared by PCR gene overlap extension (Horton et al., (1990) *Biotechniques* 8:528–535). The Adenovirus 5 fiber tail, shaft, and head regions, amino acids 1 to 581, are connected with a tandem repeat of the apoE-LDL receptor binding domain, amino acids 141 to 155. The DNA encoding ApoE is registered as Genbank accession nos. K00396 and X00199. This tandem repeat has been shown to interact efficiently with the LDL receptor (Dyer and Curtiss (1991) *J. Biol. Chem.* 266:22803–22806, incorporated herein by reference). The 5F:apoE chimera can be modified further by substitution or deletion of selected amino acid residues in the head region of the adenovirus 5 fiber protein such that the interaction with the normal adenovirus 5 cellular receptor is abolished using methods as described in McClelland, et al., *Proc. Nat. Acad. Sci.*, Vol. 88, pgs. 7993–7997 (1991), incorporated herein by reference. The primers which are used in the PCR construction are as follows:

5F: P1 5'-ATGGAGATCTTACTGAAGGCACAGCCTATA-3' (SEQ ID NO: 9)

ApoE: P2 5'-CCGCTTACGCAGCTTGCGCAGTTCTTGGGCAATGTATGAAAA-3' (SEQ ID NO: 10)
P3 5'-GTCATCGGCATCGCGGAGGAGCCGCTTACGCAGCTTGCGCAG-3'(SEQ ID NO: 11)
P4 5'-CTTACGCAGCTTGCGCAGCAGGTCATCGGCATCGCGGAGGAG-3' (SEQ ID NO: 12)
P5 5'-ATCTTCATCGCGGAGGAGCCGCTTACGCAGCTTGCGCAGCAG-3' (SEQ ID NO: 13)
P6 5'-TTAATGGAATCCTTACAGGTCATCGGCATCGCGGAGGAGCCG-3' (SEQ ID NO: 14)

The primers P1 and P2 are designed to amplify a portion of the Adenovirus 5 fiber gene, nucleotides 1920 to 2221, Genebank # M18369. The primers P1 and P6 are designed to include Bgl II and Eco RI restriction enzyme sites, respectively, for cloning into the expression vector, pGEM5F. (FIG. 2) The template which is used for amplifying the appropriate sequences is pGEM5F which contains the correct cDNA for the Adenovirus 5 fiber gene. The PCR reactions are carried out as follows: 5 min—92° C., then 45 sec—92° C., 45 sec—55° C., 2 min—72° C. for 30 cycles and then 8 min—72° C. The PCR products then are analyzed on a 1% agarose tris/acetate/EDTA gel. The expected 0.322 Kb 5F:apoE fragment can be excised from the gel and the second PCR reaction is carried out as described using primers P1 and P3 to add on the appropriate apoE sequences onto the Adenovirus 5 fiber. A total of five PCR reactions are carried out using primer P1 with each of primers P2, P3, P4, P5, and P6 in succession to generate a tandem repeat of the apoE-LDL receptor binding domain. The PCR generated 5F:apoE fragment then is cloned into the full length Adenovirus 5 fiber construct, pGEM5F, using the Bgl II and Eco RI restriction enzyme sites to form pGEM5F::apoE. (FIG. 13). The nucleotide sequence of the cloned insert then is determined by DNA sequencing and a clone having a perfect match with the expected sequence can be selected.

B. In vitro Expression and Analysis of the 5F:apoE Chimera

Expression and function of the 5F:apoE chimera is analyzed in an in vitro transcription/translation cell binding experiment using an adaptation of the surface receptor binding assay described by Leone et al. (1992) Cell. 71:479–488. A 1 μg aliquot of the pGEM5F:apoE DNA is used in the in vitro transcription/translation reaction (Promega) using [$^{35}$-S] L-methionine. Protein sample preparation for SDS PAGE analysis is carried out such that the trimeric state of the 5F:apoE chemera will remain intact (Novelli et al., (1991) *J. Biol. Chem.* 266: 9299–9303). The translated protein products are analyzed by nondenaturing 4/15% SDS PAGE and fluorography. The expected molecular weights for 5F:apoE monomer and trimer are 63 kDa and 189 kDa, respectively. Correct trimer conformation can be assessed by reactivity with monoclonal antibodies either specific to Adenovirus 5 fiber trimer, 2A6:36 and 4D2–5, or to the apoE-LDL receptor binding domain. The function of the 5F:apoE trimer then is assessed by interaction with cell surface LDL receptors. The cell surface binding assays are carried out using LDL receptor positive and negative cell lines such as CHO and CHO1d1A7 cells, respectively (Herz and Gerard (1993) *PNAS U.S.A.* 90:2812–2816), incoporated herein by reference. Normal human fibroblasts and other cell lines which express the LDL receptor may also be used in this assay. Approximately $1\times10^6$ cells will be plated onto 60 mm tissue culture dishes and are allowed to attach overnight at 37° C. in a 5% $CO_2$ atmosphere. The labeled protein mixture from the in vitro transcription/translation is applied to the cell surface monolayer and is allowed to incubate for one hour at room temperature. The cell surface is washed extensively and the cells are lyzed to analyze cell associated labeled protein. Samples are prepared for nondenaturing 4/15% SDS PAGE and fluorography. A functional 5F:apoE chimeric protein trimer will interact with CHO cells but not with CHO1d1A7 cells.

Specificity of receptor binding is demonstrated through competition analysis using human LDL, purified human apoE, and anti-apoE or anti-LDL receptor antibodies as competitors. In the presence of excess competitor the 5F:apoE trimer will not interact with the surface LDL receptors on CHO cells.

C. Incorporation of 5F:apoE Chimera into Adenovirus

The modified 5F:apoE fiber then is incorporated into adenovirus.

Figure 14:
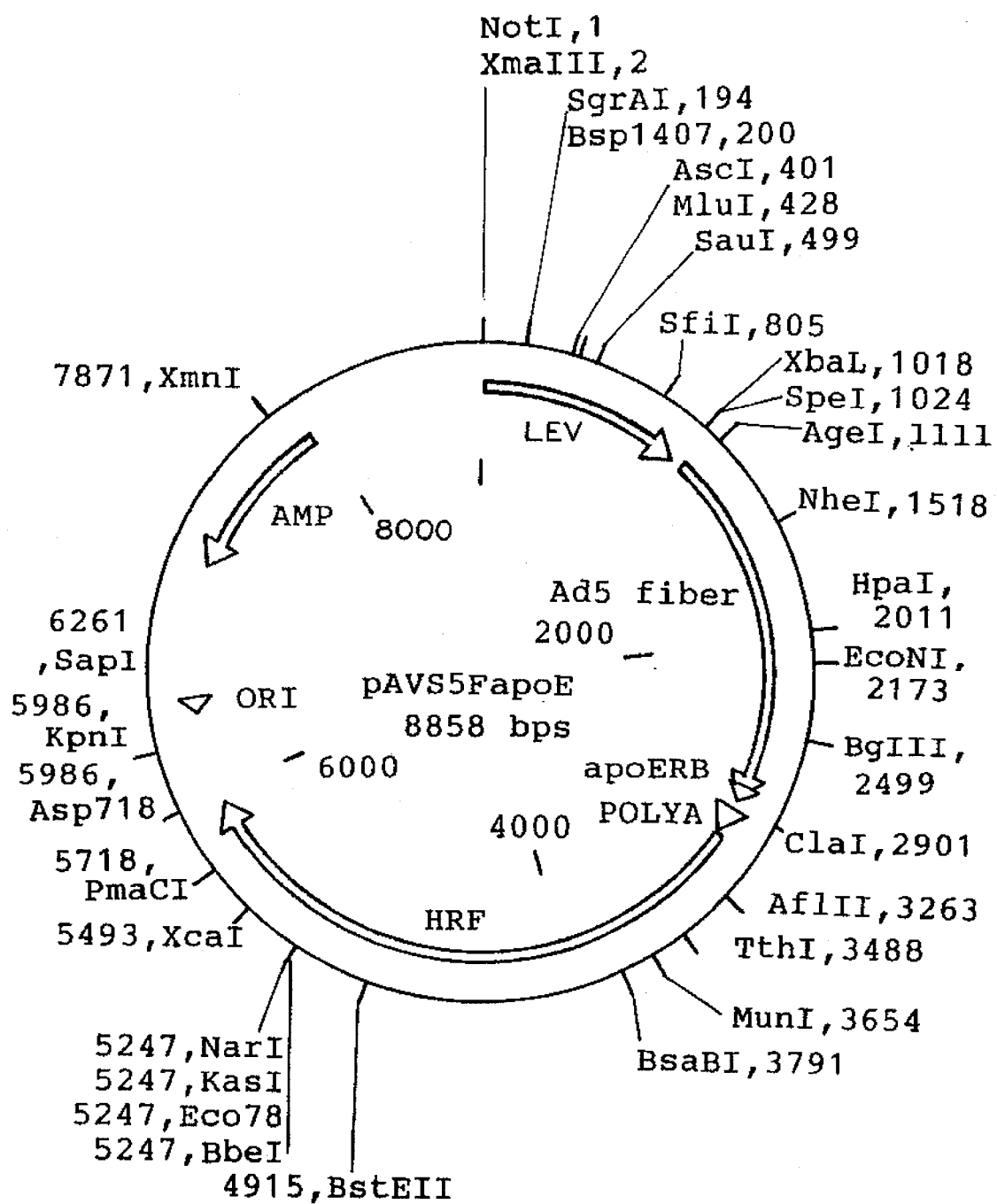
FIG. 14 is a map of plasmid pAVS5F::apoE.

The 5F:apoE chimeric construct is cloned into the shuttle vector pAVS6 (FIG. 9). pGEM5F::apoE is digested with EcoRI and BssHII to isolate the 5F:apoE fragment. The ends of the fragment are filled in with Klenow DNA polymerase to form a blunt ended 5F:apoE fragment. The blunt ended 5F:apoE fragment is then cloned into EcoRV digested pAVS6 to form pAVS5F::apoE. (FIG. 14.) pAVS5F::apoE and Cla I digested Ad 5 dl 1021 (Falgout, et al., 1987) are co-transfected into 293 cells using calcium phosphate precipitation. Homologous recombination produces a recombinant adenoviral vector particle containing the 5F:apoE gene.

The function of the recombinant 5F:apoE adenovirus is assessed by infection and cell receptor binding assays. To assess virus:LDL receptor interaction and infectivity, plaque assays, cellular receptor binding, and/or competition assays are carried out using the purified adenovirus as the receptor ligand and purified apoE or anti-LDL receptor antibodies as competitors. An infectious recombinant adenovirus expressing 5F:apoE protein which interacts with the LDL receptor will not infect cells in the presence of excess competitor.

For in vitro transduction of cells, an aliquot of the infectious viral particles containing up to about $10^{14}$ plaque forming units is added to cells expressing the LDL receptor, such as, for example, liver cells, and the viral particles are allowed to bind to the cells. For in vivo transduction of cells, an aliquot of the infectious viral particles containing up to about $10^{14}$ plaque forming units, is administered by intravenous infusion, whereby such infectious viral particles will infect cells expressing the LDL receptor, such as liver cells, for example.

EXAMPLE 3

Construction of Adenovirus 5 Including a Chimeric Fiber of Adenovirus 5 Fiber Protein and ApoE, and a Factor IX Gene

Figure 15:
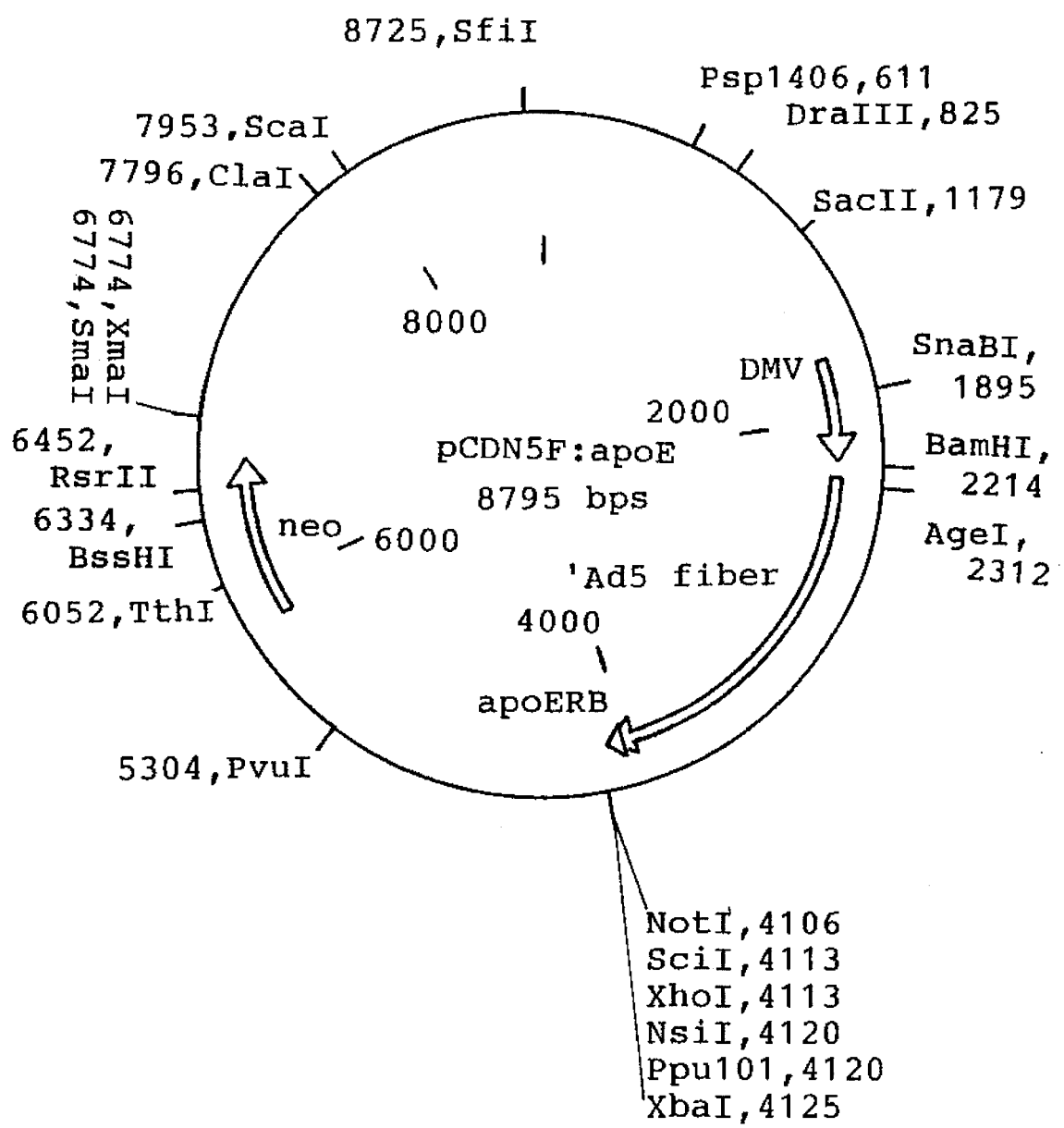
FIG. 15 is a map of plasmid pCDN5F::apoE.

A. Construction of pCDN5F:apoE pGEM5F:apoE is digested with EcoRI and BssHII to isolate the 5F:apoE fragment. The ends of the 5F:apoE fragment are treated with Klenow DNA polymerase to create blunt ends. The blunt ended 5F:apoE fragment is cloned into EcoRV digested pcDNA-neo to created pCDN5F:apoE. (FIG. 15).

Figure 16:
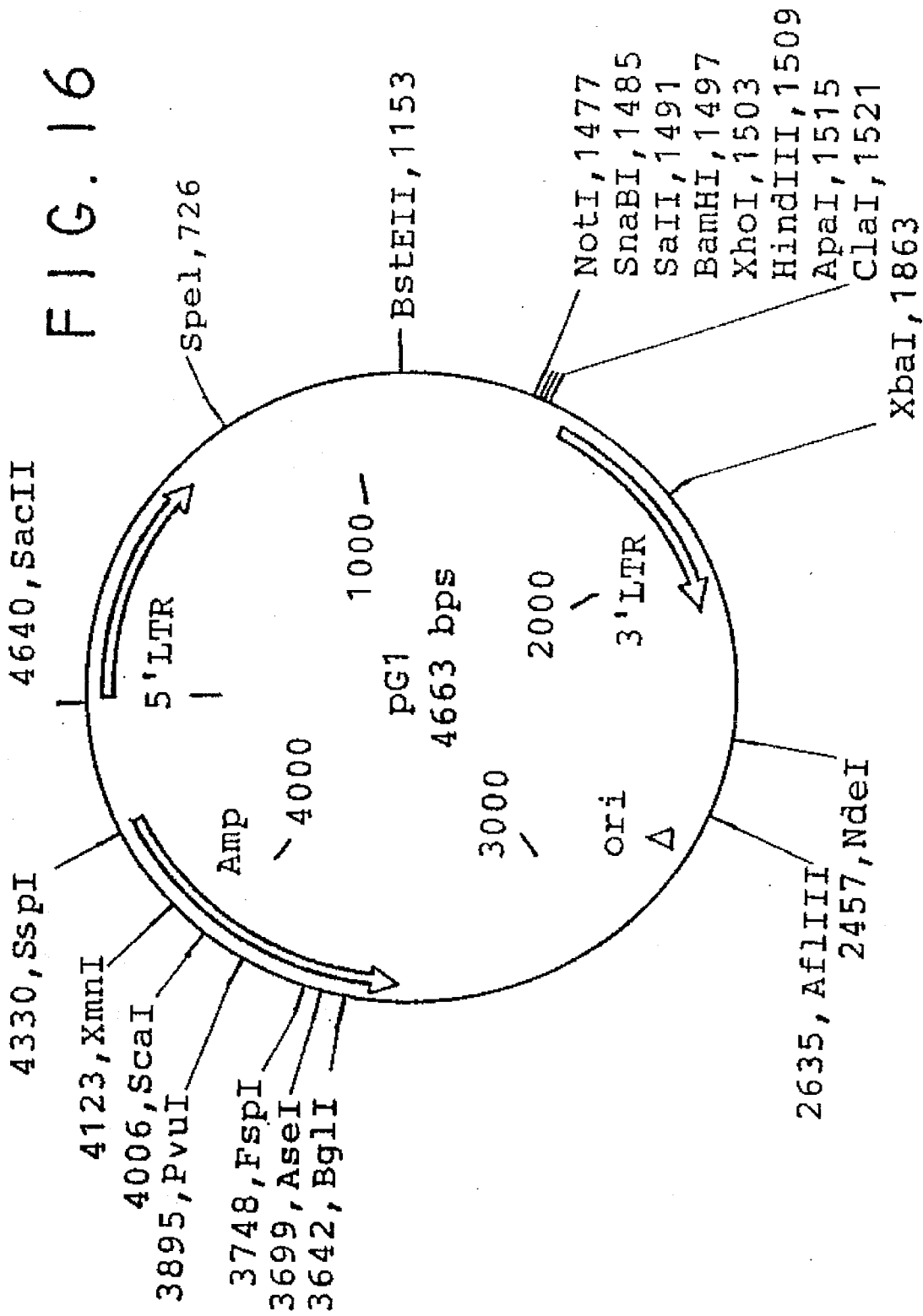
FIG. 16 is a map of plasmid pG1.
Figure 17:
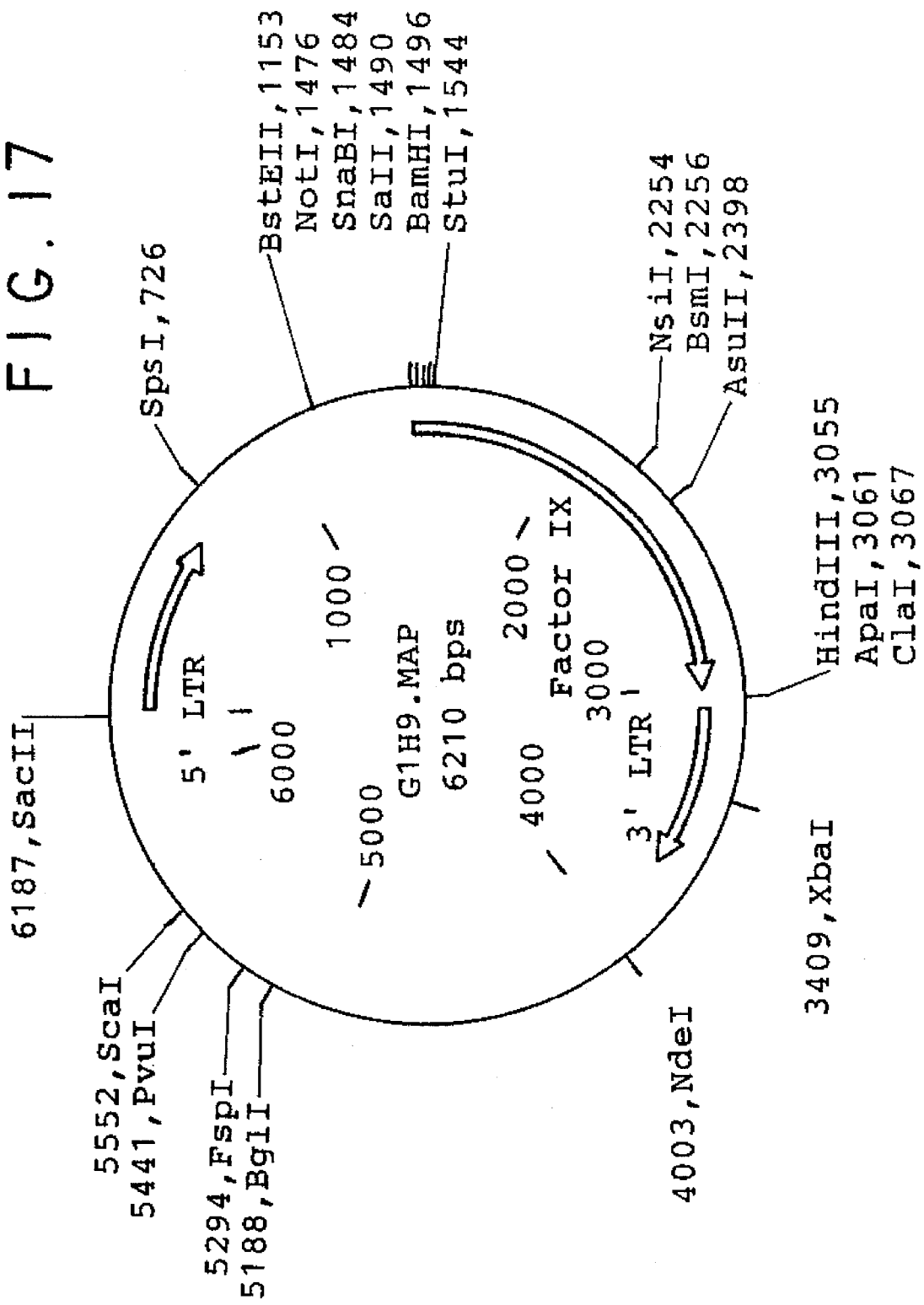
FIG. 17 is a map of plasmid pG1H9.

B. Construction of pG1H9 pG1 (described in PCT application No. WO91/10728 published Jul. 25, 1991) (FIG. 16) is cut with BamHI and HindIII. pL1XSN (Palmer, et al, *Blood,* Vol. 73, No. 2, pgs. 438–445 (February 1989), incorporated herein by reference), which contains a Factor IX gene, an SV40 promoter, and a neo$^R$gene, is also cut with BamHI and HindIII. The resulting BamHI-HindIII fragment, which contains the Factor IX gene, is then ligated to the BamHI-HindIII digested pG1 to form pG1H9. (FIG. 17).

Figure 18:
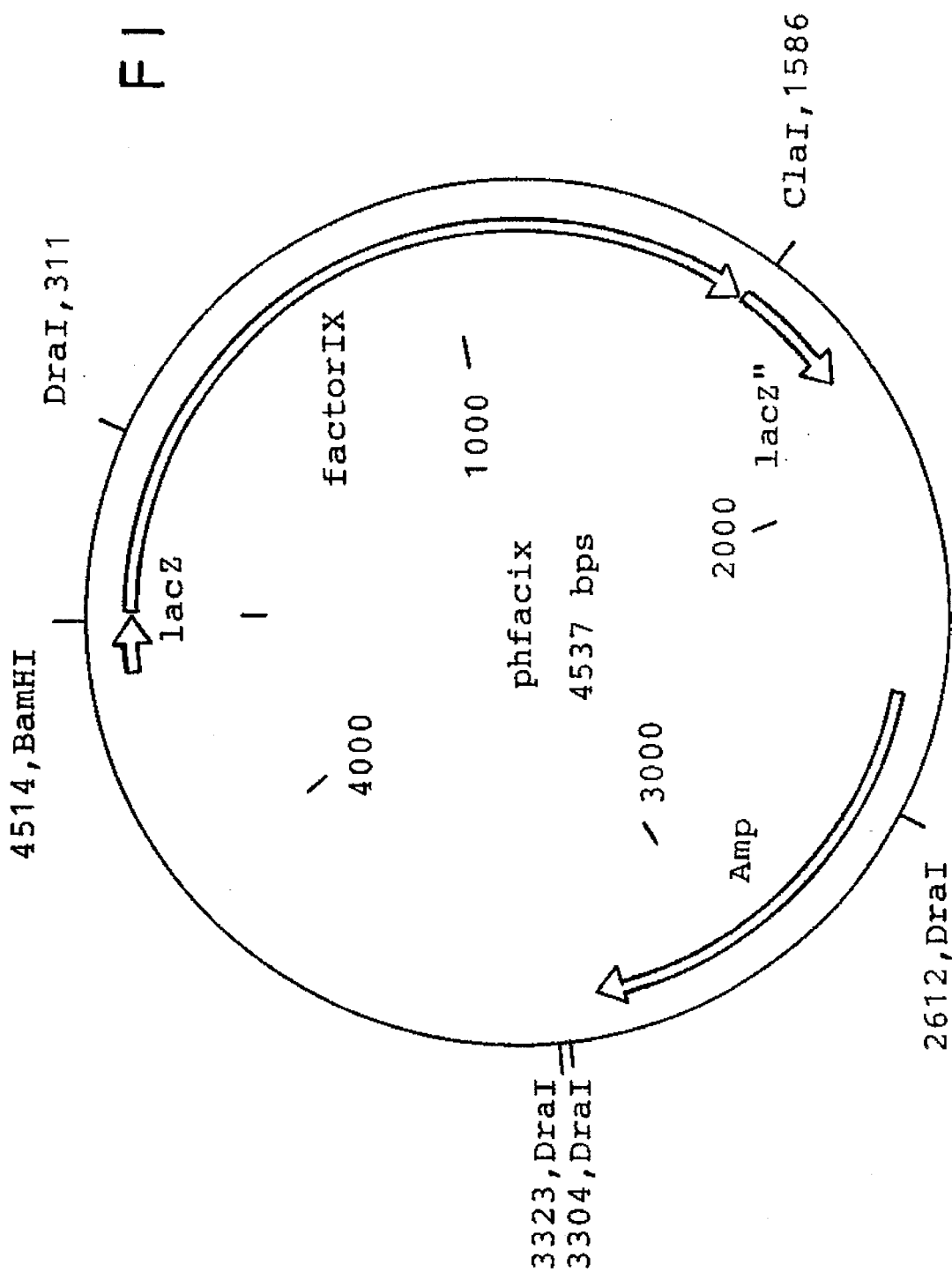
FIG. 18 is a map of plasmid phfacIX.
Figure 19:
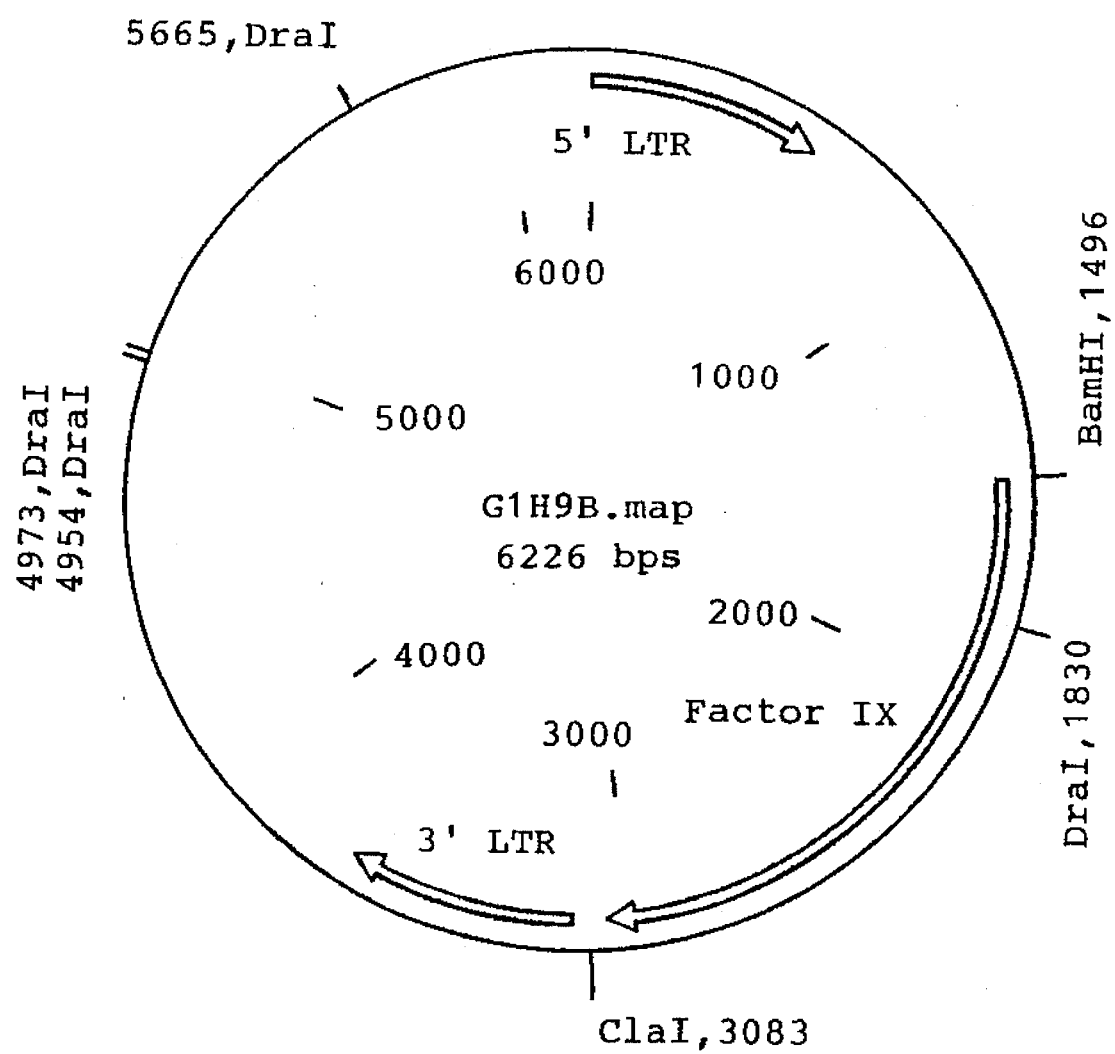
FIG. 19 is a map of plasmid pG1H9B.

C. Construction of pG1H9B pG1H9B (FIG. 19) was constructed so that the 5' untranslated region of the human Factor IX cDNA is identical to the natural 5' untranslated region. Such is not the case for pG1H9 because of an inversion in the DNA sequence.

pG1H9B was constructed as follows. First, a cDNA clone of human Factor IX was generated by PCR amplification of human liver cDNA followed by subcloning into the plasmid pBluescript SK-(Stratagene). The resulting plasmid was designated phfacIX (FIG. 18). phfacIX then was cut with BamHI and DraI, and the 334 bp fragment corresponding to the 5' end of the Factor IX cDNA was isolated. pG1H9 was cut with DraI and ClaI and the 1253 bp fragment encoding the 3' end of the Factor IX cDNA was isolated. The two isolated DNA fragments encoding Factor IX cDNA were ligated into the pG1H9 backbone which had been cut with BamHI and ClaI to generate pG1H9B (FIG. 19).

D. Construction of AVS6H9B

Factor IX cDNA (FIG. 20), which contains the entire protein coding sequence, 26 base pairs of 5' untranslated DNA (assuming translation starts at the third ATG of the message) and 160 base pairs of 3' untranslated DNA, was excised from pG1H9B by restriction digestion with ClaI, followed by filling in the 5' overhang using Klenow, followed by restriction digestion with SmaI.

Figure 21:
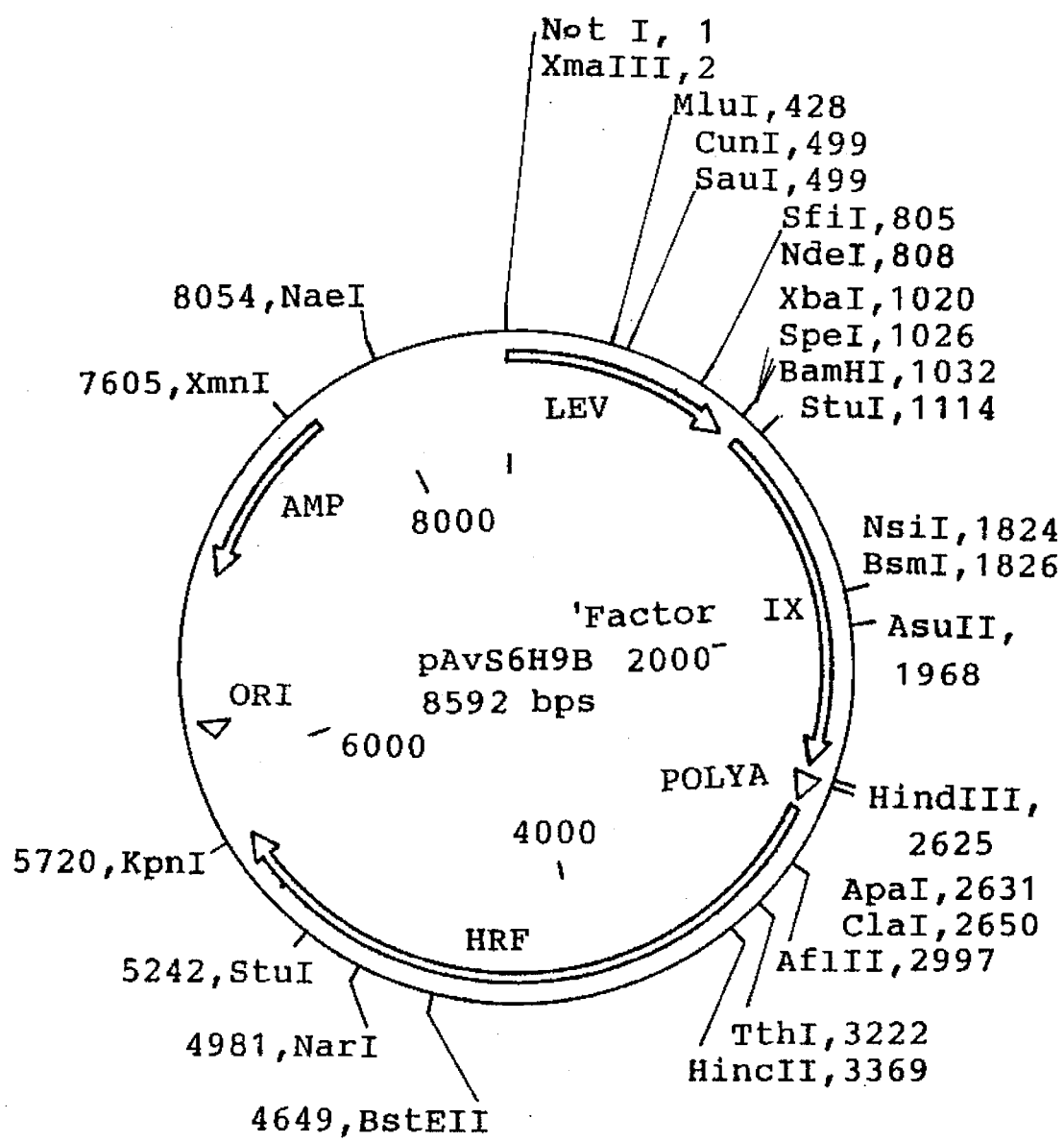
FIG. 21 is a map of plasmid pAVS6H9B.

The fragment encoding Factor IX was isolated by electrophoresis in a 1.0% agarose gel followed by electroelution of the DNA. This fragment was subcloned into pAVS6 which had been linearized with EcoRV and treated with calf intestinal phosphatase. The resulting shuttle plasmid pAvS6H9B (FIG. 21), contains the 5' inverted terminal repeat of adenovirus type 5 (Ad 5), the origin of replication of Ad 5, the Ad 5 encapsidation signal, the E1a enhancer, the RSV promoter, the tripartite leader sequence of Ad 5, Factor IX cDNA, the SV40 early polyadenylation signal, and Ad 5 sequences from nucleotide positions 3329–6246.

In order to generate a recombinant 5F:apoE adenovirus containing human Factor IX cDNA, 293 cells are transfected with pCDN5F::apoE, Cla I digested Ad 5 dl1021DNA (Falgout, et al., 1987), and pAVS6H9B digested with NotI and KpnI. The transfection is carried out by calcium phosphate precipitation, and infectious viral particles are generated which incorporate the 5F:apoE chimeric protein, and a gene encoding human Factor IX.

For in vitro transduction of cells, an aliquot of the infectious viral particles containing up to about $10^{14}$ plaque forming units is added to cells expressing the LDL receptor, such as, for example, liver cells, and the viral particles are allowed to bind to the cells. Upon transfection, the cells express Factor IX in vitro. For in vivo transduction of cells, an aliquot of the infectious viral particles containing up to about $10^{14}$ plaque forming units, is administered by intravenous infusion, such as, for example, by pottal vein infusion, whereby such infectious viral particles will infect cells expressing the LDL receptor, such as liver cells, for example. Once the liver cells are transfected with the invectious viral particles, the liver cells will express Factor IX in vivo.

It is to be understood, however, that the scope of the present invention is not to be limited to the specific embodiments described above. The invention may be practiced other than as particularly described and still be within the scope of the accompanying claims.

What is claimed is:

1. An adenovirus wherein at least a portion of the adenovirus fiber protein is removed and replaced with a ligand which is specific for a receptor located on a desired cell type.

2. An adenovirus including a fusion protein of an adenovirus fiber protein and a ligand which is specific for a receptor located on a desired cell type.

3. The adenovirus of claim 1 wherein said adenovirus fiber protein includes a head portion and a shaft portion, and said portion of the adenovirus fiber protein which is removed and replaced with a ligand which is specific for a receptor found on a desired cell type is at least a portion of the head portion.

4. The adenovirus of claim 1 wherein said adenovirus is Adenovirus 3, and amino acid residues 132 to 319 of the fiber of adenovirus 3 are removed and replaced with a ligand which is specific for a receptor located on a desired cell type.

5. The adenovirus of claim 1 wherein said adenovirus is Adenovirus 5, and amino acid residues 400 to 581 of the fiber of Adenovirus 5 are removed and replaced with a ligand which is specific for a receptor located on a desired cell type.

6. The adenovirus of claim 1 wherein said adenovirus is Adenovirus 41, and amino acid residues 387 to 563 of the long fiber of Adenovirus 41 are removed and replaced with a ligand which is specific for a receptor located on a desired cell type.

7. The adenovirus of claim 1 wherein said adenovirus is Adenovirus 41, and amino acid residues 231 to 387 of the short fiber of Adenovirus 41 are removed and replaced with a ligand which is specific for a receptor located on a desired cell type.

8. The adenovirus of claim 1 wherein said ligand is the LDL receptor binding region of the apolipoprotein E molecule.

9. The adenovirus of claim 1 wherein said ligand is epidermal growth factor.

10. The adenovirus of claim 1 wherein said ligand is fibroblast growth factor.

11. The adenovirus of claim 1 wherein said ligand is PDGF.

12. The adenovirus of claim 1 wherein said ligand is colony stimulating factor.

13. The adenovirus of claim 1 wherein said ligand is IGF-I.

14. The adenovirus of claim 1 wherein in said ligand is IGF-II.

15. The adenovirus of claim 1 wherein said ligand is selected from the group consisting of Interleukin 1,; Interleukin-2; Interleukin-3; Interleukin-4; Interleukin-5; Interleukin-6; Interleukin-7; Interleukin-8; Interleukin-9; Interleukin-10; Interleukin-11; Interleukin-12; Interleukin-13; and Interleukin-14.

16. The adenovirus of claim 1 wherein said ligand is TNF-alpha.

17. The adenovirus of claim 1 wherein said ligand is TNF-beta.

18. The adenovirus of claim 1 wherein said ligand is transferrin.

19. The adenovirus of claim 1 wherein said ligand is alpha-2-macroglobulin.

20. The adenovirus of claim 1 wherein said ligand is alpha-1 acid glycoprotein.

21. The adenovirus of claim 1 wherein said ligand is mannose-containing peptide.

22. The adenovirus of claim 1 wherein said ligand is sialyl-Lewis-X antigen-containing peptide.

23. The adenovirus of claim 1 wherein said ligand is a CD34 ligand.

24. The adenovirus of claim 1 wherein said ligand is a CD40 ligand.

25. The adenovirus of claim 1 wherein said ligand is ICAM-1.

26. The adenovirus of claim 1 wherein said ligand is M-CSF.

27. The adenovirus of claim 1 wherein said ligand is circumsporozoite protein.

28. The adenovirus of claim 1 wherein said ligand is VLA-4.

29. The adenovirus of claim 1 wherein said ligand is LFA-1.

30. The adenovirus of claim 1 wherein said ligand is NGF.

31. The adenovirus of claim 1 wherein said ligand is HIV gp120.

32. The adenovirus of claim 1 wherein said ligand is Class II MHC antigen.

33. The adenovirus of claim 1 wherein said ligand is an Fv antigen-binding domain of an immunoglobulin.

34. An adenoviral vector wherein DNA encoding a portion of the fiber protein of the adenovirus is removed and is replaced with DNA encoding a ligand which is specific for a receptor located on a desired cell type.

35. An adenoviral vector including a DNA sequence comprised of DNA encoding an adenovirus fiber protein operatively linked to DNA encoding a ligand which is specific for a receptor located on a desired cell type.

* * * * *

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 1:

CATTGTGTCG ACACCATGAA GCGCGAAGA CCGTCTGAA     39

( 2 ) INFORMATION FOR SEQ ID NO: 2:

( i ) SEQUENCE CHARACTERISTICS:
        ( A ) LENGTH: 48 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 2:

CGGGGTTCGA GAAGATGATC TGACGGTCCA CAAAGTTAGC TTATCATT     48

( 2 ) INFORMATION FOR SEQ ID NO: 3:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 3:

GTCAGATCAT CTTCTCGAAC CCCG     24

( 2 ) INFORMATION FOR SEQ ID NO: 4:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 4:

ATGTCTAGAT CACAGGGCAA TGATCCCAAA GTAGACCTG     39

( 2 ) INFORMATION FOR SEQ ID NO: 5:

( i ) SEQUENCE CHARACTERISTICS:
        ( A ) LENGTH: 38 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 5:

CATCTGCAGC ATGAAGCGCG CAAGACCGTC TGAAGATA                    38

( 2 ) INFORMATION FOR SEQ ID NO: 6:

( i ) SEQUENCE CHARACTERISTICS:
        ( A ) LENGTH: 38 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 6:

CAGGAATTCT TATTCTTGGG CAATGTATGA AAAAGTGT                    38

( 2 ) INFORMATION FOR SEQ ID NO: 7:

( i ) SEQUENCE CHARACTERISTICS:
        ( A ) LENGTH: 44 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 7:

GCAGATCTTT CCGCAGCAGC CGCCACCATG AGCATGAAAG CATC             44

( 2 ) INFORMATION FOR SEQ ID NO: 8:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 8:

GCGTCGACTC GAGTCACAGG GCAATGATCC                             30

( 2 ) INFORMATION FOR SEQ ID NO: 9:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 9:

ATGGAGATCT TACTGAAGGC ACAGCCTATA                             30

( 2 ) INFORMATION FOR SEQ ID NO: 10:

( i ) SEQUENCE CHARACTERISTICS:
        ( A ) LENGTH: 42 bases
        ( B ) TYPE: nucleic acid
        ( C ) STRANDEDNESS: single
        ( D ) TOPOLOGY: linear ( i i ) MOLECULE TYPE: PCR DNA primer ( x i ) SEQUENCE DESCRIPTION: SEQ ID NO: 10:

CCGCTTACGC AGCTTGCGCA GTTCTTGGGC AATGTATGAA AA               42

( 2 ) INFORMATION FOR SEQ ID NO: 11:

( i ) SEQUENCE CHARACTERISTICS:
    ( A ) LENGTH: 42 bases
    ( B ) TYPE: nucleic acid
    ( C ) STRANDEDNESS: single
    ( D ) TOPOLOGY: linear ( i i ) MOLECULE TYPE: PCR DNA primer ( x i ) SEQUENCE DESCRIPTION: SEQ ID NO: 11:

GTCATCGGCA TCGCGGAGGA GCCGCTTACG CAGCTTGCGC AG 42

( 2 ) INFORMATION FOR SEQ ID NO: 12:

( i ) SEQUENCE CHARACTERISTICS:
    ( A ) LENGTH: 42 bases
    ( B ) TYPE: nucleic acid
    ( C ) STRANDEDNESS: single
    ( D ) TOPOLOGY: linear ( i i ) MOLECULE TYPE: PCR DNA primer ( x i ) SEQUENCE DESCRIPTION: SEQ ID NO: 12:

CTTACGCAGC TTGCGCAGCA GGTCATCGGC ATCGCGGAGG AG 42

( 2 ) INFORMATION FOR SEQ ID NO: 13:

( i ) SEQUENCE CHARACTERISTICS:
    ( A ) LENGTH: 42 bases
    ( B ) TYPE: nucleic acid
    ( C ) STRANDEDNESS: single
    ( D ) TOPOLOGY: linear ( i i ) MOLECULE TYPE: PCR DNA primer ( x i ) SEQUENCE DESCRIPTION: SEQ ID NO: 13:

ATCTTCATCG CGGAGGAGCC GCTTACGCAG CTTGCGCAGC AG 42

( 2 ) INFORMATION FOR SEQ ID NO: 14:

( i ) SEQUENCE CHARACTERISTICS:
    ( A ) LENGTH: 42 bases
    ( B ) TYPE: nucleic acid
    ( C ) STRANDEDNESS: single
    ( D ) TOPOLOGY: linear ( i i ) MOLECULE TYPE: PCR DNA primer ( x i ) SEQUENCE DESCRIPTION: SEQ ID NO: 14:

TTAATGGAAT CCTTACAGGT CATCGGCATC GCGGAGGAGC CG 42

( 2 ) INFORMATION FOR SEQ ID NO: 15:

( i ) SEQUENCE CHARACTERISTICS:
    ( A ) LENGTH: 1548 bases
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: Factor IX cDNA ( x i ) SEQUENCE DESCRIPTION: SEQ ID NO: 15:

AGGTTATGCA GCGCGTGAAC ATGATCATGG CAGAATCACC AGGCCTCATC ACCATCTGCC 60

TTTTAGGATA TCTACTCAGT GCTGAATGTA CAGTTTTTCT TGATCATGAA AACGCCAACA 120

AAATTCTGAA TCGGCCAAAG AGGTATAATT CAGGTAAATT GGAAGAGTTT GTTCAAGGGA 180

ACCTTGAGAG AGAATGTATG GAAGAAAAGT GTAGTTTTGA AGAAGCACGA GAAGTTTTTG 240

-continued

| | | | | | | |
|---|---|---|---|---|---|---|
| AAAACACTGA | AAGAACAACT | GAATTTTGGA | AGCAGTATGT | TGATGGAGAT | CAGTGTGAGT | 300 |
| CCAATCCATG | TTTAAATGGC | GGCAGTTGCA | AGGATGACAT | TAATTCCTAT | GAATGTTGGT | 360 |
| GTCCCTTTGG | ATTTGAAGGA | AAGAACTGTG | AATTAGATGT | AACATGTAAC | ATTAAGAATG | 420 |
| GCAGATGCGA | GCAGTTTTGT | AAAAATAGTG | CTGATAACAA | GGTGGTTTGC | TCCTGTACTG | 480 |
| AGGGATATCG | ACTTGCAGAA | AACCAGAAGT | CCTGTGAACC | AGCAGTGCCA | TTTCCATGTG | 540 |
| GAAGAGTTTC | TGTTTCACAA | ACTTCTAAGC | TCACCCGTGC | TGAGACTGTT | TTTCCTGATG | 600 |
| TGGACTATGT | AAATTCTACT | GAAGCTGAAA | CCATTTTGGA | TAACATCACT | CAAAGCACCC | 660 |
| AATCATTTAA | TGACTTCACT | CGGGTTGTTG | GTGGAGAAGA | TGCCAAACCA | GGTCAATTCC | 720 |
| CTTGGCAGGT | TGTTTTGAAT | GGTAAAGTTG | ATGCATTCTG | TGGAGGCTCT | ATCGTTAATG | 780 |
| AAAAATGGAT | TGTAACTGCT | GCCCACTGTG | TTGAAACTGG | TGTTAAAATT | ACAGTTGTCG | 840 |
| CAGGTGAACA | TAATATTGAG | GAGACAGAAC | ATACAGAGCA | AAAGCGAAAT | GTGATTCGAA | 900 |
| TTATTCCTCA | CCACAACTAC | AATGCAGCTA | TTAATAAGTA | CAACCATGAC | ATTGCCCTTC | 960 |
| TGGAACTGGA | CGAACCCTTA | GTGCTAAACA | GCTACGTTAC | ACCTATTTGC | ATTGCTGACA | 1020 |
| AGGAATACAC | GAACATCTTC | CTCAAATTTG | GATCTGGCTA | TGTAAGTGGC | TGGGGAAGAG | 1080 |
| TCTTCCACAA | AGGGAGATCA | GCTTTAGTTC | TTCAGTACCT | TAGAGTTCCA | CTTGTTGACC | 1140 |
| GAGCCACATG | TCTTCGATCT | ACAAAGTTCA | CCATCTATTA | CAACATGTTC | TGTGCTGGCT | 1200 |
| TCCATGAAGG | AGGTAGAGAT | TCATGTCAAG | GAGATAGTGG | GGGACCCCAT | GTTACTGAAG | 1260 |
| TGGAAGGGAC | CAGTTTCTTA | ACTGGAATTA | TTAGCTGGGG | TGAAGAGTGT | GCAATGAAAG | 1320 |
| GCAAATATGG | AATATATACC | AAGGTATCCC | GGTATGTCAA | CTGGATTAAG | GAAAAAACAA | 1380 |
| AGCTCACTTA | ATGAAAGATG | GATTTCCAAG | GTTAATTCAT | TGGAATTGAA | AATTAACAGG | 1440 |
| GCCTCTCACT | AACTAATCAC | TTTCCCATCT | TTTGTTAGAT | TTGAATATAT | ACATTCTATG | 1500 |
| ATCATTGCTT | TTTCTCTTTA | CAGGGGAGAA | TTTCATATTT | TACCTGAG | | 1548 |